US010579912B2

(12) United States Patent
Holtmann

(10) Patent No.: US 10,579,912 B2
(45) Date of Patent: Mar. 3, 2020

(54) USER REGISTRATION FOR INTELLIGENT ASSISTANT COMPUTER

(71) Applicant: Microsoft Technology Licensing, LLC, Redmond, WA (US)

(72) Inventor: Michelle Lynn Holtmann, Kent, WA (US)

(73) Assignee: MICROSOFT TECHNOLOGY LICENSING, LLC, Redmond, WA (US)

(*) Notice: Subject to any disclaimer, the term of this patent is extended or adjusted under 35 U.S.C. 154(b) by 127 days.

(21) Appl. No.: 15/682,425

(22) Filed: Aug. 21, 2017

(65) Prior Publication Data

US 2018/0232201 A1 Aug. 16, 2018

Related U.S. Application Data

(60) Provisional application No. 62/459,020, filed on Feb. 14, 2017, provisional application No. 62/482,165, filed on Apr. 5, 2017.

(51) Int. Cl.
*G06K 9/72* (2006.01)
*G06K 9/00* (2006.01)
(Continued)

(52) U.S. Cl.
CPC ............ *G06K 9/726* (2013.01); *A61B 5/0205* (2013.01); *A61B 5/0507* (2013.01); *G01S 5/18* (2013.01);
(Continued)

(58) Field of Classification Search
CPC ........... G06K 9/00214; G06K 9/00255; G06K 9/00261; G06K 9/00288; G06K 9/00295;
(Continued)

(56) References Cited

U.S. PATENT DOCUMENTS 6,067,673 A 5/2000 Paese et al.
6,119,088 A 9/2000 Ciluffo
(Continued)

FOREIGN PATENT DOCUMENTS

EP 2947476 A1 11/2015
GB 2522922 A 8/2015
(Continued)

OTHER PUBLICATIONS

"Non Final Office Action Issued in U.S. Appl. No. 15/636,422", dated Sep. 4, 2018, 11 Pages.
(Continued)

*Primary Examiner* — Daniel G Mariam
(74) *Attorney, Agent, or Firm* — Alleman Hall Creasman & Tuttle LLP

(57) ABSTRACT

Registration of a person with an intelligent assistant computer includes obtaining one or more image frames captured via one or more cameras that depict an initially unregistered person. Facial recognition data for the initially unregistered person is extracted from the one or more image frames. A spoken command to register the initially unregistered person is received via one or more microphones. Upon determining that the spoken command originated from the registered person having the pre-established registration privilege, the initially unregistered person is registered as a newly registered person by associating one or more additional privileges with the facial recognition data in a person profile for the newly registered person.

20 Claims, 13 Drawing Sheets

(51) Int. Cl.

| | |
|---|---|
| G06T 7/70 | (2017.01) |
| G06K 9/62 | (2006.01) |
| G06F 3/16 | (2006.01) |
| G10L 15/18 | (2013.01) |
| G06N 20/00 | (2019.01) |
| G06T 7/73 | (2017.01) |
| G06T 7/246 | (2017.01) |
| G01S 5/18 | (2006.01) |
| G06T 7/60 | (2017.01) |
| G10L 15/22 | (2006.01) |
| G10L 15/28 | (2013.01) |
| H04R 1/40 | (2006.01) |
| H04R 3/00 | (2006.01) |
| H04N 5/33 | (2006.01) |
| H04N 7/18 | (2006.01) |
| G10L 15/02 | (2006.01) |
| G06N 5/02 | (2006.01) |
| G06N 5/04 | (2006.01) |
| G10L 15/06 | (2013.01) |
| G10L 15/24 | (2013.01) |
| G06F 17/27 | (2006.01) |
| G10L 15/26 | (2006.01) |
| G10L 15/19 | (2013.01) |
| G10L 15/08 | (2006.01) |
| G10L 15/32 | (2013.01) |
| G10L 25/51 | (2013.01) |
| H04L 29/06 | (2006.01) |
| A61B 5/0205 | (2006.01) |
| A61B 5/05 | (2006.01) |
| G01S 13/72 | (2006.01) |
| G06F 21/35 | (2013.01) |
| G07C 9/00 | (2020.01) |
| G08B 13/14 | (2006.01) |
| G06F 3/01 | (2006.01) |
| G06F 3/0482 | (2013.01) |
| G06F 3/0484 | (2013.01) |
| H04N 21/231 | (2011.01) |
| G06F 3/0488 | (2013.01) |
| G06F 16/70 | (2019.01) |
| H04N 5/247 | (2006.01) |
| G01S 13/38 | (2006.01) |
| G01S 13/88 | (2006.01) |

(52) U.S. Cl.
CPC ............ *G01S 13/726* (2013.01); *G06F 3/017* (2013.01); *G06F 3/0482* (2013.01); *G06F 3/04842* (2013.01); *G06F 3/167* (2013.01); *G06F 17/271* (2013.01); *G06F 21/35* (2013.01); *G06K 9/00214* (2013.01); *G06K 9/00255* (2013.01); *G06K 9/00288* (2013.01); *G06K 9/00295* (2013.01); *G06K 9/00342* (2013.01); *G06K 9/00711* (2013.01); *G06K 9/6254* (2013.01); *G06K 9/6255* (2013.01); *G06K 9/6289* (2013.01); *G06K 9/6296* (2013.01); *G06N 5/025* (2013.01); *G06N 5/047* (2013.01); *G06N 20/00* (2019.01); *G06T 7/248* (2017.01); *G06T 7/60* (2013.01); *G06T 7/70* (2017.01); *G06T 7/74* (2017.01); *G07C 9/00111* (2013.01); *G08B 13/1427* (2013.01); *G10L 15/02* (2013.01); *G10L 15/063* (2013.01); *G10L 15/08* (2013.01); *G10L 15/18* (2013.01); *G10L 15/1815* (2013.01); *G10L 15/1822* (2013.01); *G10L 15/19* (2013.01); *G10L 15/22* (2013.01); *G10L 15/24* (2013.01); *G10L 15/26* (2013.01); *G10L 15/28* (2013.01); *G10L 15/32* (2013.01); *G10L 25/51* (2013.01); *H04L 63/102* (2013.01); *H04N 5/332* (2013.01); *H04N 7/181* (2013.01); *H04N 21/231* (2013.01); *H04R 1/406* (2013.01); *H04R 3/005* (2013.01); *G01S 13/38* (2013.01); *G01S 13/888* (2013.01); *G06F 3/0488* (2013.01); *G06F 16/70* (2019.01); *G06K 2209/09* (2013.01); *G06T 2207/20101* (2013.01); *G06T 2207/30196* (2013.01); *G06T 2207/30204* (2013.01); *G10L 2015/0635* (2013.01); *G10L 2015/088* (2013.01); *G10L 2015/223* (2013.01); *G10L 2015/225* (2013.01); *H04N 5/247* (2013.01)

(58) Field of Classification Search
CPC .......... G06K 9/00342; G06K 9/00362; G06K 9/00711; G06K 9/00973; G06K 9/6254; G06K 9/6255; G06K 9/6289; G06K 9/6296; G06K 9/726; G06F 21/35; G06F 17/271; G06F 17/279; G06F 1/324; G06F 21/32; G06F 3/017; G06F 3/011; G06F 3/0304; G06F 3/0482; G06F 3/167; A61B 5/1113; A61B 5/117; A61B 5/7475; G01S 5/18; G01S 5/28; G01S 13/726; G06N 20/00; G06T 7/248; G06T 7/292; G06T 7/70; G06T 7/74
USPC ...................................................... 382/118
See application file for complete search history.

(56) References Cited

U.S. PATENT DOCUMENTS

| | | |
|---|---|---|
| 6,332,122 B1 | 12/2001 | Ortega et al. |
| 6,442,524 B1 | 8/2002 | Ecker et al. |
| 6,477,500 B2 | 11/2002 | Maes |
| 6,496,799 B1 | 12/2002 | Pickering |
| 6,574,601 B1 | 6/2003 | Brown et al. |
| 6,727,925 B1 | 4/2004 | Bourdelais |
| 6,728,679 B1 | 4/2004 | Strubbe et al. |
| 6,816,730 B2 | 11/2004 | Davies et al. |
| 6,873,953 B1 | 3/2005 | Lennig |
| 7,019,749 B2 | 3/2006 | Guo et al. |
| 7,050,110 B1 | 5/2006 | Lienhart et al. |
| 7,330,566 B2 | 2/2008 | Cutler |
| 7,475,010 B2 | 1/2009 | Chao |
| 7,610,365 B1 | 10/2009 | Kraft et al. |
| 7,716,056 B2 | 5/2010 | Weng et al. |
| 7,803,050 B2 | 9/2010 | Mao et al. |
| 8,139,945 B1 | 3/2012 | Amir et al. |
| 8,165,087 B2 | 4/2012 | Panabaker |
| 8,170,875 B2 | 5/2012 | Hetherington et al. |
| 8,213,689 B2 | 7/2012 | Yagnik et al. |
| 8,265,252 B2 | 9/2012 | Ducheneaut et al. |
| 8,326,627 B2 | 12/2012 | Kennewick et al. |
| 8,340,975 B1 | 12/2012 | Rosenberger |
| 8,374,879 B2 | 2/2013 | Falcon et al. |
| 8,453,402 B2 | 6/2013 | Huang |
| 8,457,959 B2 | 6/2013 | Kaiser |
| 8,543,402 B1 | 9/2013 | Ma |
| 8,639,762 B2 | 1/2014 | Rasmussen et al. |
| 8,644,842 B2 | 2/2014 | Arrasvuori et al. |
| 8,712,758 B2 | 4/2014 | Crouch et al. |
| 8,752,145 B1 * | 6/2014 | Dotan ................. H04L 63/0861 340/5.2 |
| 8,762,150 B2 | 6/2014 | Edgington et al. |
| 8,762,156 B2 | 6/2014 | Chen |
| 8,779,965 B2 | 7/2014 | Sentelle et al. |
| 8,805,691 B2 | 8/2014 | Genly |
| 8,861,924 B2 | 10/2014 | Meads et al. |
| 8,862,156 B2 | 10/2014 | Bell et al. |
| 8,903,128 B2 | 12/2014 | Shet et al. |
| 8,913,103 B1 | 12/2014 | Sargin et al. |
| 8,942,986 B2 | 1/2015 | Cheyer et al. |

(56) References Cited

U.S. PATENT DOCUMENTS

| | | |
|---|---|---|
| 8,949,359 B2 | 2/2015 | Rasmussen et al. |
| 9,037,601 B2 | 5/2015 | Palay |
| 9,085,303 B2 | 7/2015 | Wolverton et al. |
| 9,119,512 B2 | 9/2015 | Martins, Jr. et al. |
| 9,171,542 B2 | 10/2015 | Gandrabur et al. |
| 9,230,544 B2 | 1/2016 | Kwon et al. |
| 9,268,406 B2 | 2/2016 | Geisner et al. |
| 9,300,925 B1 | 3/2016 | Zhang |
| 9,307,355 B2 | 4/2016 | Nehrenz et al. |
| 9,311,932 B2 | 4/2016 | Carter |
| 9,318,105 B1 | 4/2016 | Khosla |
| 9,348,990 B2 | 5/2016 | Chuaprasert et al. |
| 9,368,114 B2 | 6/2016 | Larson et al. |
| 9,378,740 B1 | 6/2016 | Rosen et al. |
| 9,380,177 B1 | 6/2016 | Rao et al. |
| 9,389,681 B2 | 7/2016 | Sankar et al. |
| 9,412,392 B2 | 8/2016 | Lindahl |
| 9,424,840 B1 | 8/2016 | Hart et al. |
| 9,466,286 B1 | 10/2016 | Hart et al. |
| 9,495,331 B2 | 11/2016 | Govrin et al. |
| 9,495,613 B2 | 11/2016 | Holz et al. |
| 9,507,977 B1 | 11/2016 | Mor et al. |
| 9,508,341 B1 | 11/2016 | Parlikar et al. |
| 9,514,227 B1 | 12/2016 | Garrett et al. |
| 9,558,749 B1 | 1/2017 | Secker-Walker et al. |
| 9,576,574 B2 | 2/2017 | van Os |
| 9,622,059 B2 | 4/2017 | Bouzid et al. |
| 9,626,352 B2 | 4/2017 | Allen et al. |
| 9,633,652 B2 | 4/2017 | Kurniawati et al. |
| 9,749,583 B1 | 8/2017 | Fineberg et al. |
| 9,761,055 B2 | 9/2017 | Miller |
| 9,767,616 B2 | 9/2017 | Miller |
| 9,842,299 B2 | 12/2017 | Stolarz et al. |
| 9,898,250 B1 | 2/2018 | Williams et al. |
| 9,965,247 B2 | 5/2018 | Jarvis et al. |
| 10,178,301 B1 * | 1/2019 | Welbourne .......... H04N 5/23219 |
| 2003/0103647 A1 | 6/2003 | Rui et al. |
| 2003/0131064 A1 | 7/2003 | Bell et al. |
| 2005/0182627 A1 | 8/2005 | Tanaka et al. |
| 2005/0216264 A1 | 9/2005 | Attwater et al. |
| 2005/0225427 A1 | 10/2005 | Bell et al. |
| 2005/0285774 A1 | 12/2005 | Wittenberg et al. |
| 2006/0028552 A1 | 2/2006 | Aggarwal et al. |
| 2007/0024487 A1 | 2/2007 | Zemany et al. |
| 2007/0100480 A1 | 5/2007 | Sinclair et al. |
| 2007/0152157 A1 | 7/2007 | Page |
| 2007/0198245 A1 | 8/2007 | Kamatani et al. |
| 2007/0271086 A1 | 11/2007 | Peters et al. |
| 2008/0030345 A1 | 2/2008 | Austin et al. |
| 2008/0071547 A1 | 3/2008 | Prieto et al. |
| 2008/0077015 A1 | 3/2008 | Boric-Lubecke et al. |
| 2008/0195387 A1 | 8/2008 | Zigel et al. |
| 2008/0288251 A1 | 11/2008 | Cooper et al. |
| 2009/0066690 A1 | 3/2009 | Harrison |
| 2009/0303342 A1 | 12/2009 | Corcoran et al. |
| 2009/0319269 A1 | 12/2009 | Aronowitz |
| 2010/0073363 A1 | 3/2010 | Densham et al. |
| 2010/0100851 A1 | 4/2010 | Clark et al. |
| 2010/0179813 A1 | 7/2010 | Summerfield et al. |
| 2010/0195906 A1 | 8/2010 | Uliyar et al. |
| 2011/0010170 A1 | 1/2011 | Burns et al. |
| 2011/0184735 A1 | 7/2011 | Flaks et al. |
| 2011/0216090 A1 | 9/2011 | Woo et al. |
| 2011/0219339 A1 | 9/2011 | Densham |
| 2011/0298967 A1 | 12/2011 | Clavin et al. |
| 2012/0026335 A1 | 2/2012 | Brown et al. |
| 2012/0253791 A1 | 10/2012 | Heck et al. |
| 2012/0265535 A1 | 10/2012 | Bryant-rich et al. |
| 2012/0268604 A1 | 10/2012 | Tree |
| 2013/0110519 A1 | 5/2013 | Cheyer et al. |
| 2013/0117377 A1 | 5/2013 | Miller |
| 2013/0212501 A1 | 8/2013 | Anderson et al. |
| 2013/0253936 A1 | 9/2013 | Harvey |
| 2013/0342568 A1 | 12/2013 | Ambrus et al. |
| 2014/0033071 A1 | 1/2014 | Gruber et al. |
| 2014/0067679 A1 | 3/2014 | O'Reilly et al. |
| 2014/0156276 A1 | 6/2014 | Nakano et al. |
| 2014/0180629 A1 | 6/2014 | Dokmanic et al. |
| 2014/0214421 A1 | 7/2014 | Shriberg et al. |
| 2014/0214429 A1 | 7/2014 | Pantel |
| 2014/0222422 A1 | 8/2014 | Sarikaya et al. |
| 2014/0244263 A1 | 8/2014 | Pontual et al. |
| 2014/0272821 A1 | 9/2014 | Pitschel et al. |
| 2014/0330569 A1 | 11/2014 | Kolavennu et al. |
| 2014/0341440 A1 | 11/2014 | Walch |
| 2014/0365226 A1 | 12/2014 | Sinha |
| 2015/0016642 A1 | 1/2015 | Walsh et al. |
| 2015/0019714 A1 | 1/2015 | Shaashua et al. |
| 2015/0025887 A1 | 1/2015 | Sidi et al. |
| 2015/0032456 A1 | 1/2015 | Wait |
| 2015/0035976 A1 | 2/2015 | Mayuzumi |
| 2015/0102996 A1 | 4/2015 | Yim et al. |
| 2015/0138332 A1 | 5/2015 | Cheng et al. |
| 2015/0149179 A1 | 5/2015 | Korbecki |
| 2015/0149182 A1 | 5/2015 | Kalns et al. |
| 2015/0162000 A1 | 6/2015 | Di censo et al. |
| 2015/0172285 A1 | 6/2015 | Lo et al. |
| 2015/0249664 A1 | 9/2015 | Talhami et al. |
| 2015/0279368 A1 | 10/2015 | Contolini et al. |
| 2015/0340033 A1 | 11/2015 | Di fabbrizio et al. |
| 2015/0347114 A1 | 12/2015 | Yoon |
| 2015/0382047 A1 | 12/2015 | Van os et al. |
| 2016/0019889 A1 | 1/2016 | Alvarez guevara et al. |
| 2016/0086018 A1 | 3/2016 | Lemoff |
| 2016/0088043 A1 | 3/2016 | Jiang et al. |
| 2016/0092732 A1 | 3/2016 | Black |
| 2016/0138247 A1 | 5/2016 | Conway et al. |
| 2016/0148417 A1 | 5/2016 | Kim et al. |
| 2016/0155443 A1 | 6/2016 | Khan et al. |
| 2016/0173293 A1 | 6/2016 | Kennedy |
| 2016/0179831 A1 | 6/2016 | Gruber et al. |
| 2016/0187961 A1 | 6/2016 | Elibol et al. |
| 2016/0203002 A1 | 7/2016 | Kannan et al. |
| 2016/0210411 A1 | 7/2016 | Mentis |
| 2016/0217783 A1 | 7/2016 | Konuma et al. |
| 2016/0225373 A1 | 8/2016 | Casado et al. |
| 2016/0234595 A1 | 8/2016 | Goran et al. |
| 2016/0234616 A1 | 8/2016 | Gateau |
| 2016/0283185 A1 | 9/2016 | Mclaren et al. |
| 2016/0342702 A1 | 11/2016 | Barve et al. |
| 2016/0358598 A1 | 12/2016 | Williams et al. |
| 2016/0360336 A1 | 12/2016 | Gross et al. |
| 2016/0380929 A1 | 12/2016 | Katis et al. |
| 2017/0013409 A1 | 1/2017 | Cerchio et al. |
| 2017/0025124 A1 | 1/2017 | Mixter et al. |
| 2017/0032021 A1 | 2/2017 | Watanachote |
| 2017/0032787 A1 | 2/2017 | Dayal |
| 2017/0039423 A1 | 2/2017 | Cork et al. |
| 2017/0039602 A1 | 2/2017 | Shi-nash et al. |
| 2017/0068423 A1 | 3/2017 | Napolitano et al. |
| 2017/0078573 A1 | 3/2017 | Chen et al. |
| 2017/0133011 A1 | 5/2017 | Chen et al. |
| 2017/0140760 A1 | 5/2017 | Sachdev |
| 2017/0185375 A1 | 6/2017 | Martel et al. |
| 2017/0194000 A1 | 7/2017 | Itani et al. |
| 2017/0230705 A1 | 8/2017 | Pardue et al. |
| 2017/0236512 A1 | 8/2017 | Williams et al. |
| 2017/0242651 A1 | 8/2017 | Lang et al. |
| 2017/0249309 A1 | 8/2017 | Sarikaya |
| 2017/0262472 A1 | 9/2017 | Goldenberg |
| 2017/0278480 A1 | 9/2017 | Sung et al. |
| 2017/0287490 A1 | 10/2017 | Biswal et al. |
| 2017/0315208 A1 | 11/2017 | Sadr |
| 2017/0322939 A1 | 11/2017 | Byron et al. |
| 2017/0359666 A1 | 12/2017 | Lyren et al. |
| 2018/0047394 A1 | 2/2018 | Tian et al. |
| 2018/0048768 A1 | 2/2018 | Spittle et al. |
| 2018/0074785 A1 | 3/2018 | Ohmura |
| 2018/0091782 A1 | 3/2018 | Bashkin |
| 2018/0096696 A1 | 4/2018 | Mixter |
| 2018/0158454 A1 | 6/2018 | Campbell et al. |
| 2018/0199123 A1 | 7/2018 | Rao et al. |
| 2018/0218080 A1 | 8/2018 | Krishnamurthy et al. |
| 2018/0231653 A1 | 8/2018 | Pradeep et al. |

(56) References Cited

U.S. PATENT DOCUMENTS

| | | | |
|---|---|---|---|
| 2018/0232563 A1 | 8/2018 | Albadawi et al. |
| 2018/0232571 A1 | 8/2018 | Bathiche et al. |
| 2018/0232608 A1 | 8/2018 | Pradeep et al. |
| 2018/0232645 A1 | 8/2018 | Finkelstein et al. |
| 2018/0232662 A1 | 8/2018 | Solomon et al. |
| 2018/0232902 A1 | 8/2018 | Albadawi et al. |
| 2018/0233132 A1 | 8/2018 | Herold et al. |
| 2018/0233139 A1 | 8/2018 | Finkelstein et al. |
| 2018/0233140 A1 | 8/2018 | Koishida et al. |
| 2018/0233141 A1 | 8/2018 | Solomon et al. |
| 2018/0233142 A1 | 8/2018 | Koishida et al. |
| 2018/0233145 A1 | 8/2018 | Bathiche et al. |
| 2018/0260680 A1 | 9/2018 | Finkelstein et al. |
| 2018/0293221 A1 | 10/2018 | Finkelstein et al. |
| 2019/0057703 A1* | 2/2019 | Zeinstra | G06F 3/167 |

FOREIGN PATENT DOCUMENTS

| | | |
|---|---|---|
| KR | 1020070016280 A | 2/2007 |
| WO | 2007018523 A2 | 2/2007 |
| WO | 2010104772 A1 | 9/2010 |
| WO | 2013061268 A2 | 5/2013 |
| WO | 2015012449 A1 | 1/2015 |
| WO | 2016114922 A1 | 7/2016 |
| WO | 2016162678 A1 | 10/2016 |
| WO | 2016205419 A1 | 12/2016 |

OTHER PUBLICATIONS

"Non Final Office Action Issued in U.S. Appl. No. 15/640,251", dated Oct. 15, 2018, 22 Pages.

"Non Final Office Action Issued in U.S. Appl. No. 15/646,871", dated Dec. 19, 2018, 22 Pages.

"Non Final Office Action Issued in U.S. Appl. No. 15/656,994", dated Jan. 22, 2019, 8 Pages.

"Non Final Office Action Issued in U.S. Appl. No. 15/657,031", dated Oct. 5, 2018, 16 Pages.

"Non-Final Office Action Issued in U.S. Appl. No. 15/657,822", dated Feb. 21, 2019, 25 Pages.

"Non Final Office Action Issued in U.S. Appl. No. 15/832,656", dated Feb. 7, 2019, 8 Pages.

"Amazon Alexa's 'Follow-Up Mode' enables successive requests without trigger word", Retrieved from: https://appleinsider.com/articles/18/03/09/amazon-alexas-follow-up-mode-enables-successive-requests-without-trigger-word, Mar. 9, 2018, 7 Pages.

"Multiple Agents (each trained for different domain) for One Chat Bot?", Retrieved from: https://discuss.api.ai/t/multiple-agents-each-trained-for-different-domain-for-one-chat-bot/1002, Jul. 1, 2016, 1 Page.

"SARA: the Socially Aware Robot Assistant", Retrieved from: https://web.archive.org/web/20160707141922/http:/articulab.hcii.cs.cmu.edu:80/projects/sara/, Jul. 7, 2017, 10 Pages.

Arsikere, et al., "Computationally-efficient Endpointing Features for Natural Spoken Interaction with Personal-assistant Systems", In Proceedings of IEEE International Conference on Acoustics, Speech and Signal Processing, May 4, 2014, pp. 3241-3245.

Ferrer, et al., "Is the Speaker Done Yet? Faster and More Accurate End-of-Utterance Detection using Prosody", In Proceedings of the 7th International Conference on Spoken Language Processing, Sep. 16, 2002, pp. 2061-2064.

Kalal, et al., "Face-TLD: Tracking-Learning-Detection Applied to Faces", In Proceedings of 17th IEEE International Conference on Image Processing, Sep. 26, 2010, pp. 3789-3792.

Kozhaya, Joe, "10 Steps to Train an Effective Chatbot and its Machine Learning Models", Retrieved from: https://developer.ibm.com/dwblog/2016/10-steps-train-chat-bot-chatbot-machine-learning/, Dec. 12, 2016, 7 Pages.

Lacharite, Noelle, "Updated: Alexa Skills Kit Fact Template: Step-by-Step Guide to Build a Fact Skill", Retrieved from https://developer.amazon.com/blogs/post/Tx3DVGG0K0TPUGQ/New-Alexa-Skills-Kit-Template:-Step-by-Step-Guide-to-Build-a-Fact-Skill, Mar. 29, 2016, 33 Pages.

Li, Bo, "A Multiple-Camera System Calibration Toolbox Using a Feature Descriptor-based Calibration Pattern", In Proceedings of IEEE International Conference on Intelligent Robots and Systems, Nov. 3, 2013, pp. 1301-1307.

Mengusoglu, Erhan, "Confidence Measures for Speech/Speaker Recognition and Applications on Turkish LVCSR", Retrieved from https://web.archive.org/web/20040619044603/http://www.tcts.fpms.ac.be/publications/phds/mengusoglu/thesis_mengus.pdf, Apr. 20, 2004, 143 Pages.

Verma et al., "Face Detection and Tracking in a Video by Propagating Detection Probabilities", In Proceedings of IEEE Transactions on Pattern Analysis and Machine Intelligence, vol. 25, Issue 10, Oct. 1, 2003, pp. 1215-1228.

Panzarino, Matthew, "Here's an Actual 3D Indoor Map of a Room Captured With Google's Project Tango Phone", Retrieved From https://techcrunch.com/2014/02/21/heres-an-actual-3d-indoor-map-of-a-room-captured-with-googles-project-tango-phone/, Feb. 21, 2014, 6 Pages.

"International Search Report and Written Opinion Issued in PCT Application No. PCT/US2018/017139", dated May 8, 2018, 13 Pages.

"International Search Report and Written Opinion Issued in PCT Application No. PCT/US2018/017140", dated May 18, 2018, 12 Pages.

"International Search Report and Written Opinion Issued in PCT Application No. PCT/US2018/017506", dated May 4, 2018, 13 Pages.

"International Search Report and Written Opinion Issued in PCT Application No. PCT/US2018/017508", dated May 8, 2018, 13 Pages.

"International Search Report and Written Opinion Issued in PCT Application No. PCT/US2018/017509", dated May 11, 2018, 11 Pages.

"International Search Report and Written Opinion Issued in PCT Application No. PCT/US2018/017510", dated Apr. 20, 2018, 14 Pages.

"International Search Report and Written Opinion Issued in PCT Application No. PCT/US2018/017511", dated May 17, 2018, 12 Pages.

"International Search Report and Written Opinion Issued in PCT Application No. PCT/US2018/017512", dated May 4, 2018, 15 Pages.

"International Search Report and Written Opinion Issued in PCT Application No. PCT/US2018/017513", dated Apr. 12, 2018, 15 Pages.

"International Search Report and Written Opinion Issued in PCT Application No. PCT/US2018/017514", dated May 17, 2018, 12 Pages.

"International Search Report and Written Opinion Issued in PCT Application No. PCT/US2018/017515", dated May 9, 2018, 12 Pages.

"International Search Report and Written Opinion Issued in PCT Application No. PCT/US2018/017517", dated May 11, 2018, 12 Pages.

Porcheron, et al., "Do Animals Have Accents?: Talking with Agents in Multi-Party Conversation", In Proceedings of the ACM Conference on Computer-Supported Cooperative Work and Social Computing, Feb. 25, 2017, 14 Pages.

Pullen, John Patrick., "Amazon Echo Tip: How to Add Multiple Users ! Time", Retrieved from http://time.com/4668359/amazon-echo-alexa-multiple-accounts/, Feb. 13, 2017, 3 Pages.

Xiang, Li, "Improving Knowledge Base Population With Information Extraction", A Thesis Submitted in Partial fulfillment of the Requirements of the University of New York for the Degree of Doctor of Philosophy, May 2016, 131 Pages.

(56) References Cited

OTHER PUBLICATIONS

Yamamoto, S, et al., "Algorithm Optimizations for Low-Complexity Eye Tracking", In Proceedings of IEEE International Conference on Systems, Man, and Cybernetics, Oct. 2009, pp. 18-22.
Yun-Nung, Chen, "Unsupervised Learning and Modeling of Knowledge and Intent for Spoken Dialogue Systems", Proceedings of the Annual Meeting of the Association for Computational Linguistics, Jul. 28, 2015, 8 Pages.
Zhang, et al., "A Joint Model of Intent Determination and Slot Filling for Spoken Language Understanding", In Proceedings of the 25th International Joint Conference on Artificial Intelligence, Jul. 9, 2016, pp. 2993-2999.
Ballan, et al., "Event Detection and Recognition for Semantic Annotation of Video", In Journal of Multimedia Tools and Applications, vol. 51, Issue 1, Nov. 10, 2010, pp. 279-302.
"Train the Natural Language Processing Classifiers", Retrieved From <<https://www.mindmeld.com/docs/train_the_natural_language_processing_classifiers.html>>, Retrieved on: May 2, 2017, 10 Pages.
"Using Multiple Alexa Devices", Retrirved From <<https://www.amazon.com/gp/help/customer/display.html?nodeId=202013740>>, Apr. 24, 2017, 2 Pages.
"Application Filed in U.S. Appl. No. 15/173,349", filed Jun. 3, 2016, 34 Pages.
"Application Filed in U.S. Appl. No. 15/395,961", filed Dec. 30, 2016, 79 Pages.
Beltagy, et al., "Improved Semantic Parsers for If-Then Statements", In Proceedings of the 54th Annual Meeting of the Association for Computational Linguistics, vol. 1, Aug. 7, 2016, pp. 726-736.
Boakye, et al., "Overlapped Speech Detection for Improved Speaker Diarization in Multiparty Meetings", In Proceedings of IEEE International Conference on Acoustics, Speech and Signal Processing, Mar. 31, 2008, 4 Pages.
Cho, et al., "A Multi-Sensor Fusion System for Moving Object Detection and Tracking in Urban Driving Environments", In IEEE International Conference on Robotics & Automation, May 31, 2014, 8 Pages.
Fossard, et al., Between Anaphora and Deixis . . . The Resolution of the Demonstrative Noun Phrase "that N", In Journal of Language and Cognitive Processes, vol. 27, Issue 9, Nov. 2, 2011, 3 Pages.
Gebhart, Andrew, "How to bring Alexa into every room of your home", Retrieved From <<https://www.cnet.com/how-to/how-to-install-alexa-in-every-room-of-your-home/>>, Feb. 2, 2017, 8 Pages.
Goncalves, et al., "Assessing Users' Emotion At Interaction Time: A Multimodal Approach With Multiple Sensors", In Proceedings of Soft Computing, vol. 21, Issue 18, Mar. 21, 2016, 8 Pages.
Goswami, et al., "A Reviewon Low Light Image Enhancement Using Image Processing Technique", In International Journal of Technical Research, vol. 5, Issue 1, Mar. 2016, pp. 60-62.
He, et al., "Sensor scheduling for target tracking: A Monte Carlo sampling approach", In Journal of Digital Signal Processing, vol. 16, Issue 5, Sep. 2006, pp. 533-545.
Huijbregts, et al., "Speech Overlap Detection in a Two-Pass Speaker Diarization System", In Proceedings of 10th Annual Conference of the International Speech Communication, Sep. 6, 2009, pp. 1063-1066.
Kabadjov, Mijail Alexandrov., "A Comprehensive Evaluation of Anaphora Resolution and Discourse-new Classitication", In thesis of University of Essex, May 2007, 266 Pages.
Kang, et al., "Detection and Tracking of Moving Objects from Overlapping EO and IR Sensors", In Conference on Computer Vision and Pattern Recognition Workshop, Jun. 27, 2004, 6 Pages.
Liu, et al., "Reliable Multiple Object Tracking under Heavy Occlusions", In Intelligence Information Processing and Trusted Computing (IPTC), 2010 International Symposium., Oct. 28, 2010, 3 Pages.

MK, et al., "Ambiguities in Natural Language Processing", In International Journal of Innovative Research in Computer and Communication Engineering, vol. 2, Special Issue 5, Oct. 2014, pp. 392-394.
Pan, et al., "Robust Occlusion Handling in Object Tracking", In IEEE Conference on Computer Vision and Pattern Recognition, Jun. 17, 2007, 8 Pages.
Quirk, et al., "Language to Code: Learning Semantic Parsers for If-This-Then-That Recipes", In Proceedings of the 53rd Annual Meeting of the Association for Computational Linguistics, Jul. 26, 2015, pp. 878-888.
Rizwan, et al., "Local Enhancement for Robust Face Detection in Poor SNR Images", In International Journal of Computer Science and Network Security, vol. 9, Issue 6, Jun. 2009, pp. 93-96.
Sinha, et al., "An Analysis Engine for Dependable Elicitation on Natural Language Use Case Description and its Application to Industrial Use Cases", In IBM Research Report, RC242712, Dec. 18, 2008, 12 Pages.
Toutanova, et al., "Compositional Learning of Embeddings for Relation Paths in Knowledge Bases and Text", In Proceedings of the 54th Annual Meeting of the Association for Computational Linguistics, Aug. 7, 2016, pp. 1434-1444.
Wagner, Martin, "Tracking with Multiple Sensors", By Faculty of Computer Science at the Technical University of Munich, Sep. 12, 2004, 202 Pages.
Wheeler, et al., "Face Recognition at a Distance", In Publication of Springer, Jan. 2011, pp. 353-381.
Zotkin, et al., "Joint Audio-Visual Tracking Using Particle Filters", In EURASIP Journal on Applied Signal Processing, vol. 2002, Issue 1, Jan. 2002, pp. 1154-1164.
"Non Provisional Application Filed in U.S. Appl. No. 15/885,518", filed Jan. 31, 2018, 40 Pages.
Constine, Jose, "Instagram launches selfie filters, copying the last big Snapchat feature", Retrieved from https://techcrunch.com/2017/05/16/instagram-face-filters/, May 16, 2017, 8 Pages.
"International Search Report and Written Opinion Issued in PCT Application No. PCT/US2019/022836", dated Jun. 24, 2019, 15 Pages.
"International Search Report and Written Opinion Issued in PCT Application No. PCT/US2019/029558", dated Jun. 28, 2019, 10 Pages.
"Non Final Office Action Issued in U.S. Appl. No. 15/682,407", dated Jun. 26, 2019,15 Pages.
Miro, et al., "Speaker Diarization: A review of Recent Research", In the Proceedings of IEEE Transactions on Audio, Speech and Language Processing, vol. 20, Issue 2, Feb. 1, 2012, 15 Pages.
Moattar, et al., "A Review on Speaker Diarization Systems and Approaches", In the Publication of Speech Communication, vol. 54, Issue 10, Dec. 12, 2010, 39 Pages.
"International Search Report & Written Opinion for PCT Patent Application No. PCT/US2018/062384", dated Feb. 15, 2019, 12 Pages.
Yu, et al., "Smart Meeting Systems: A Survey of State of the Art and Open Issues", In the Proceedings of ACM Computing Surveys, vol. 42, No. 2, Mar. 5, 2010, 20 Pages.
"Non-Final Office Action Issued in U.S. Appl. No. 15/646,871", dated Sep. 3, 2019, 23 Pages.
"Final Office Action Issued in U.S. Appl. No. 15/832,656", dated Aug. 23, 2019, 10 Pages.
"Final Office Action Issued in U.S. Appl. No. 15/657,822", dated Aug. 22, 2019, 22 Pages.
"Final Office Action Issued in U.S. Appl. No. 15/640,251", dated Apr. 2, 2019, 22 Pages.
"Final Office Action Issued in U.S. Appl. No. 15/646,871", dated Apr. 19, 2019, 22 Pages.
"Non Final Office Action Issued in U.S. Appl. No. 15/640,251", dated Sep. 12, 2019, 21 Pages.
"Notice of Allowance Issued in U.S. Appl. No. 16/573,677", dated Nov. 6, 2019, 9 Pages.

\* cited by examiner

USER REGISTRATION FOR INTELLIGENT ASSISTANT COMPUTER

CROSS REFERENCE TO RELATED APPLICATIONS

This application claims priority to U.S. Provisional Patent Application No. 62/459,020 filed Feb. 14, 2017, and to U.S. Provisional Patent Application No. 62/482,165 filed Apr. 5, 2017, the entirety of which are hereby incorporated herein by reference.

BACKGROUND

Intelligent assistant computers may provide users with voice interaction, music playback, weather or news information, and a search interface to name just a few examples. Intelligent assistant computers may offer access to some information to multiple persons of a household or workplace. However, other information provided by intelligent assistant computers may be private to a particular individual, such as inbound communications, for example.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

Registration of a person with an intelligent assistant computer includes obtaining one or more image frames captured via one or more cameras that depict an initially unregistered person. Facial recognition data for the initially unregistered person is extracted from the one or more image frames. A spoken command to register the initially unregistered person is received via one or more microphones. Upon determining that the spoken command originated from a registered person having a pre-established registration privilege, the initially unregistered person is registered as a newly registered person by associating one or more additional privileges with the facial recognition data in a person profile for the newly registered person. The additional privileges may permit the newly registered person to initiate one or more operations performed by the intelligent assistant computer that were not previously permitted prior to registration.

DETAILED DESCRIPTION

Figure 1:
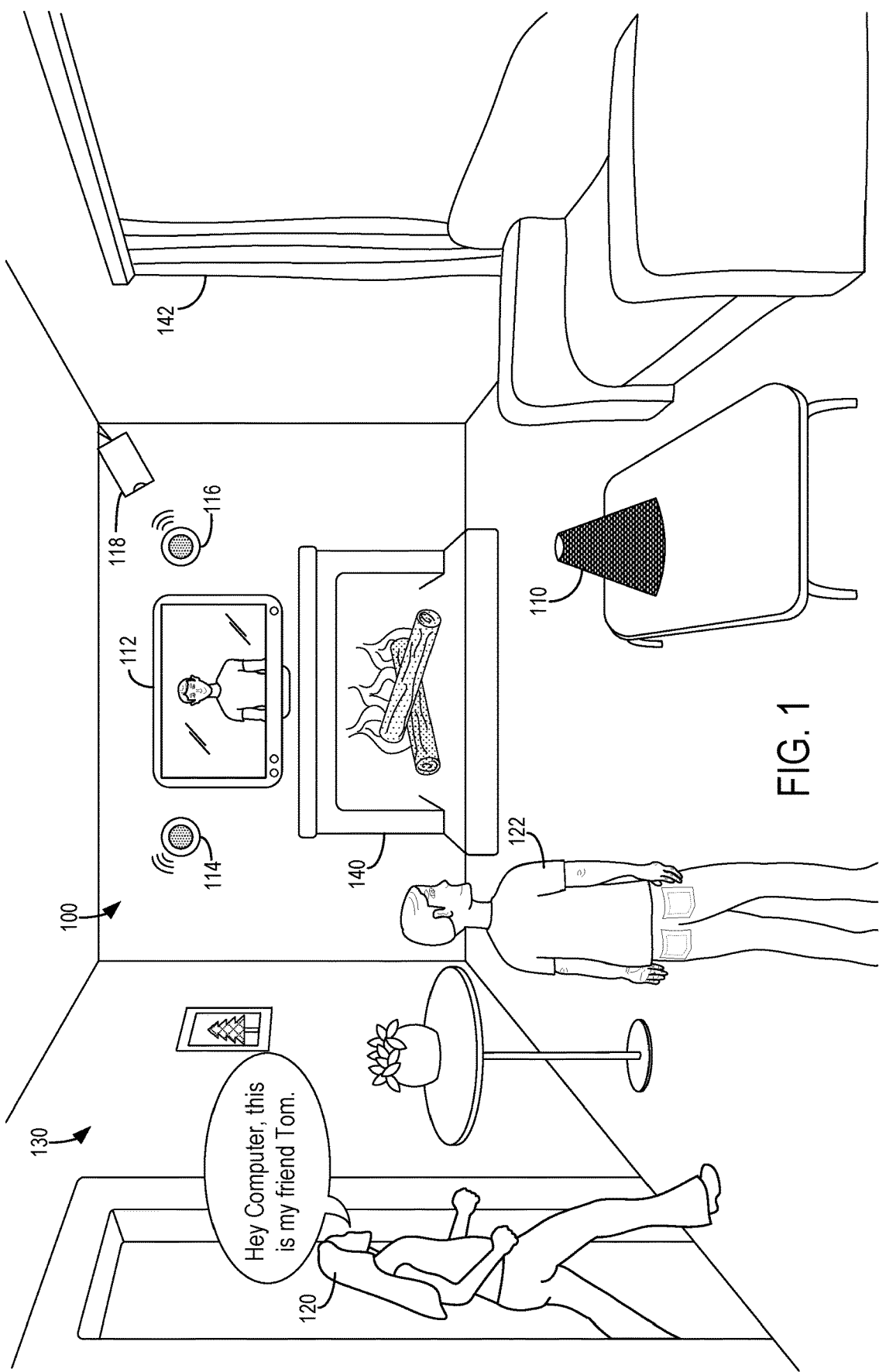
FIG. 1 depicts an example use-environment of an intelligent assistant computing system.

FIG. 1 depicts an example use-environment of an intelligent assistant computing system 100. In this example, a first person 120 introduces a second person 122 to computing system 100 by speaking aloud a phrase that is captured by the computing system via a microphone. For example, first person 120 is depicted in FIG. 1 speaking the phrase: "Hey Computer, this is my friend Tom", referring to second person 122. This introduction by first person 120 may be used to initiate registration of second person 122 with respect to computing system 100.

Registration of users with traditional computing systems can be cumbersome and frustrating for some users. Typically, an administrative user is tasked with navigating non-intuitive menus and settings of a computer program within a graphical user interface. A natural language interface supported by the intelligent assistant computing system disclosed herein enables a user to register new users by introducing those new users to the computing system using intuitive human-to-human introductions. For example, the new person's name and/or relationship status to the registered person may be announced to the computing system through a spoken phrase to register a new person. In this way, users may engage with the computing system in an intuitive manner that is more akin to a human-based interaction.

In this example, first person 120 is registered with computing system 100, and may be referred to as a registered person or user with regards to the computing system. For example, first person 120 may be an owner, a primary user, or an administrative user of computing system 100 that has previously engaged in a registration operation with regards to the computing system. Persons registered with computing system 100 may obtain additional privileges with respect to the computing system, as will be described in further detail herein. By contrast, second person 122 is initially unregistered with computing system 100, and may be referred to as an initially unregistered person or user with regards to the computing system. For example, second person 122 may be a guest that is visiting first person 120 at a location 130 that is monitored by computing system 100. In this example, location 130 is a living room within a residence of first person 120.

Intelligent assistant computing system 100 includes one or more computing devices that provide an intelligent assistant service. Accordingly, computing system 100 includes at least an intelligent assistant computing device 110 that provides the intelligent assistant service—i.e., an intelligent assistant computer. In at least some implementations, computing device 110 may take the form of an on-premises, all-in-one intelligent assistant computing device. Computing device 110 may include one or more graphical display devices, one or more audio speakers, one or more microphones, one or more cameras, etc. that are integrated with and/or located on-board the computing device or its enclosure.

However, in at least some implementations, computing device 110 may be one of a plurality of components of intelligent assistant computing system 100. For example, computing system 100 may include one or more other computing devices, graphical display devices, audio speakers, microphones, cameras, etc. in addition to computing device 110. FIG. 1 depicts an example of a graphical display device 112, audio speakers 114 and 116, and camera 118 of computing system 100 that are located on-premises with regards to location 130, yet are physically separate from computing device 110. Computing system 100 may include one or more computing devices that are located at different locations of the same premises and/or remotely located from the premises (e.g., cloud-based servers). Computing device 110 may be operatively connected with one or more other devices using wired and/or wireless connections. For example, computing device 110 may be communicatively coupled to one or more other computing devices, sensor devices, or controlled devices via a communications network using any suitable set of wired and/or wireless communications protocols.

As described in further detail herein, computing system 100 may be configured to detect the presence of persons within a monitored region, individually track the spatial location of those persons, communicate with those persons, individually identify those persons using image data captured via one or more cameras and/or audio data captured via one or more microphone, among other sensor inputs. Computing system 100 may be configured to receive and process natural language inputs, such as spoken phrases, for example.

A person acting in the role of a user may utilize intelligent assistant features supported by computing system 100 for myriad functions. For example, the user may provide natural language input (e.g., a spoken command) to direct computing system 100 to perform a variety of operations, such as providing an informational response to a query, sending or presenting a communication message, presenting audio/video content, capturing and storing image or audio content, transferring an instance of a user session from one device to another, or controlling other devices to name just a few examples. Some or all of these various operations may be associated with privileges that are not available to all users, such as unregistered persons, for example. The user may, for example, ask computing system 100 for information about a wide range of topics, such as weather, personal calendar events, movie show times, etc. As another example, the user may control other devices via computing system 100, such as graphical display device 112, audio speakers 114 and 116, a gas fireplace 140, or motorized curtains 142. As yet another example, computing system 100 may be utilized to receive and store messages and/or reminders to be delivered at an appropriate future time.

Figure 2:
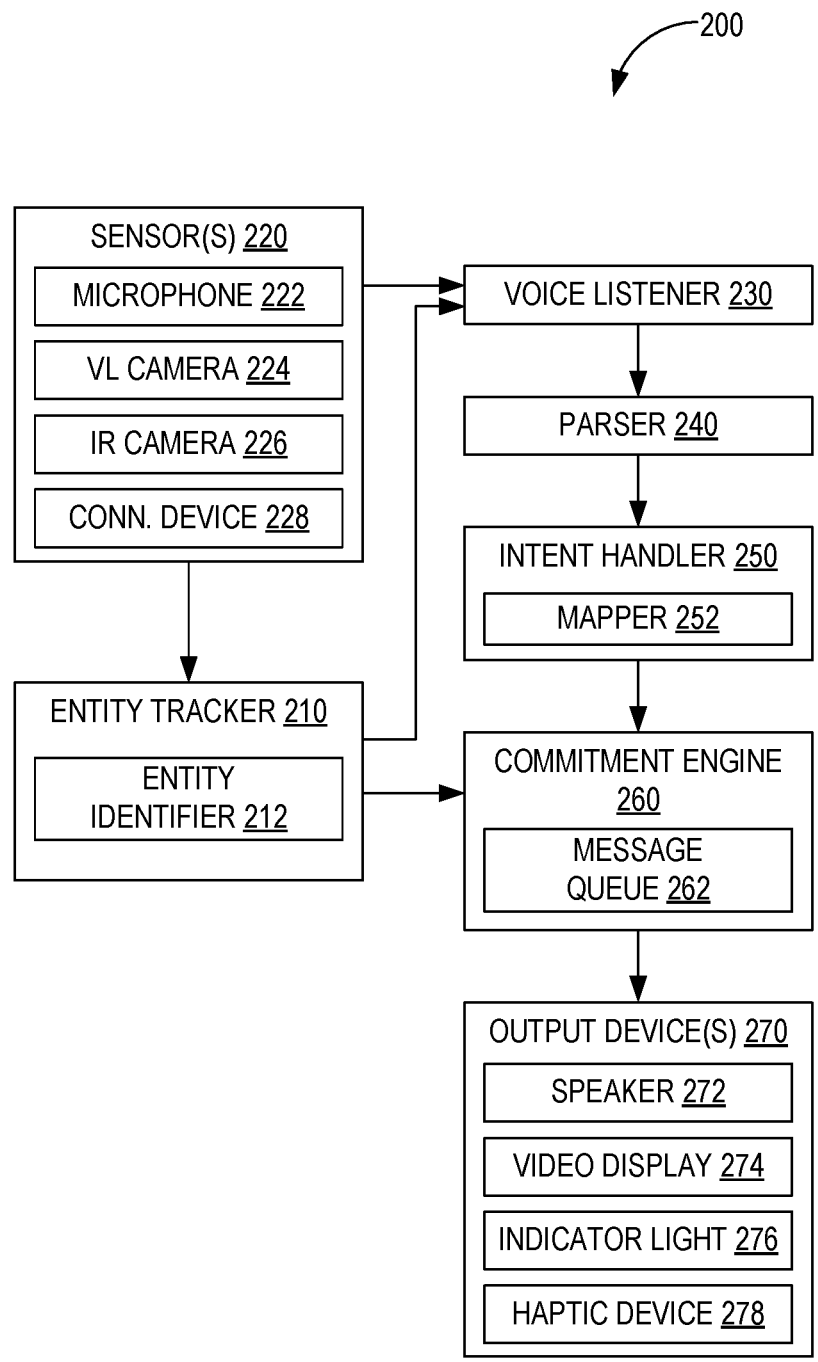
FIG. 2 is a schematic diagram depicting an example intelligent assistant computing system.

FIG. 2 is a schematic diagram depicting an example intelligent assistant computing system 200 that provides an intelligent assistant service. Computing system 200 is a non-limiting example of computing system 100 of FIG. 1. Computing system 200 is capable of recognizing and responding to natural language inputs. As similarly described with reference to computing system 100 of FIG. 1, computing system 200 may be implemented as a single computing device or as two or more devices. Two or more devices of computing system 200 may be distributed at different locations of a premises to be served by the intelligent assistant service and/or two or more devices of the computing system be geographically distributed (e.g., in a cloud-supported network configuration).

Computing system 200 includes at least one sensor 220, an entity tracker 210, a voice listener 230, a parser 240, an intent handler 250, a commitment engine 260, and at least one output device 270. In some examples the sensors 220 may include one or more microphones 222, visible light cameras 224, infrared cameras 226, and connectivity devices 228, such as Wi-Fi or Bluetooth modules. In some examples sensor(s) 220 may comprise stereoscopic and/or depth cameras, head trackers, eye trackers, accelerometers, gyroscopes, gaze detection devices, electric-field sensing componentry, GPS or other location tracking devices, temperature sensors, device state sensors, and/or any other suitable sensor.

The entity tracker 210 is configured to detect entities and their activities, including people, animals, or other living things, as well as non-living objects. Entity tracker 210 includes an entity identifier 212 that is configured to recognize individual users and/or non-living objects. Voice listener 230 receives audio data and utilizes speech recognition functionality to translate spoken utterances into text. Voice listener 230 also may assign confidence value(s) to the translated text, and may perform speaker recognition to determine an identity of the person speaking, as well as assign probabilities to the accuracy of such identifications. Parser 240 analyzes text and confidence values received from voice listener 230 to derive user intentions and generate corresponding machine-executable language.

Intent handler 250 receives machine-executable language representing user intentions from the parser 240, and resolves missing and ambiguous information to generate commitments. Commitment engine 260 stores commitments from the intent handler 250. At a contextually appropriate time, the commitment engine may deliver one or more messages and/or execute one or more actions that are associated with one or more commitments. Commitment engine 260 may store messages in a message queue 262 or cause one or more output devices 270 to generate output. The output devices 270 may comprise one or more of speaker(s) 272, video display(s) 274, indicator light(s) 276, haptic device(s) 278, and/or other suitable output devices. In other examples, output devices 270 may comprise one or more other devices or systems, such as home lighting, thermostats, media programs, door locks, etc., that may be controlled via actions executed by the commitment engine 260.

In different examples the voice listener 230, parser 240, intent handler 250, commitment engine 260, and/or entity tracker 210 may be embodied in software that is stored in memory and executed by one or more processors of a computing device. In some implementations, specially programmed logic processors may be utilized to increase the computational efficiency and/or effectiveness of the intelligent assistant computer.

In some examples the voice listener 230 and/or commitment engine 260 may receive context information including associated confidence values from entity tracker 210. As described in more detail below, entity tracker 210 may determine an identity, position, and/or current status of one or more entities within range of one or more sensors, and may output such information to one or more other modules, such as voice listener 230, commitment engine 260, etc. In some examples, entity tracker 210 may interpret and evaluate sensor data received from one or more sensors, and may output context information based on the sensor data. Context information may include the entity tracker's guesses/predictions as to the identity, position, and/or status of one or more detected entities based on received sensor data.

Figure 3:
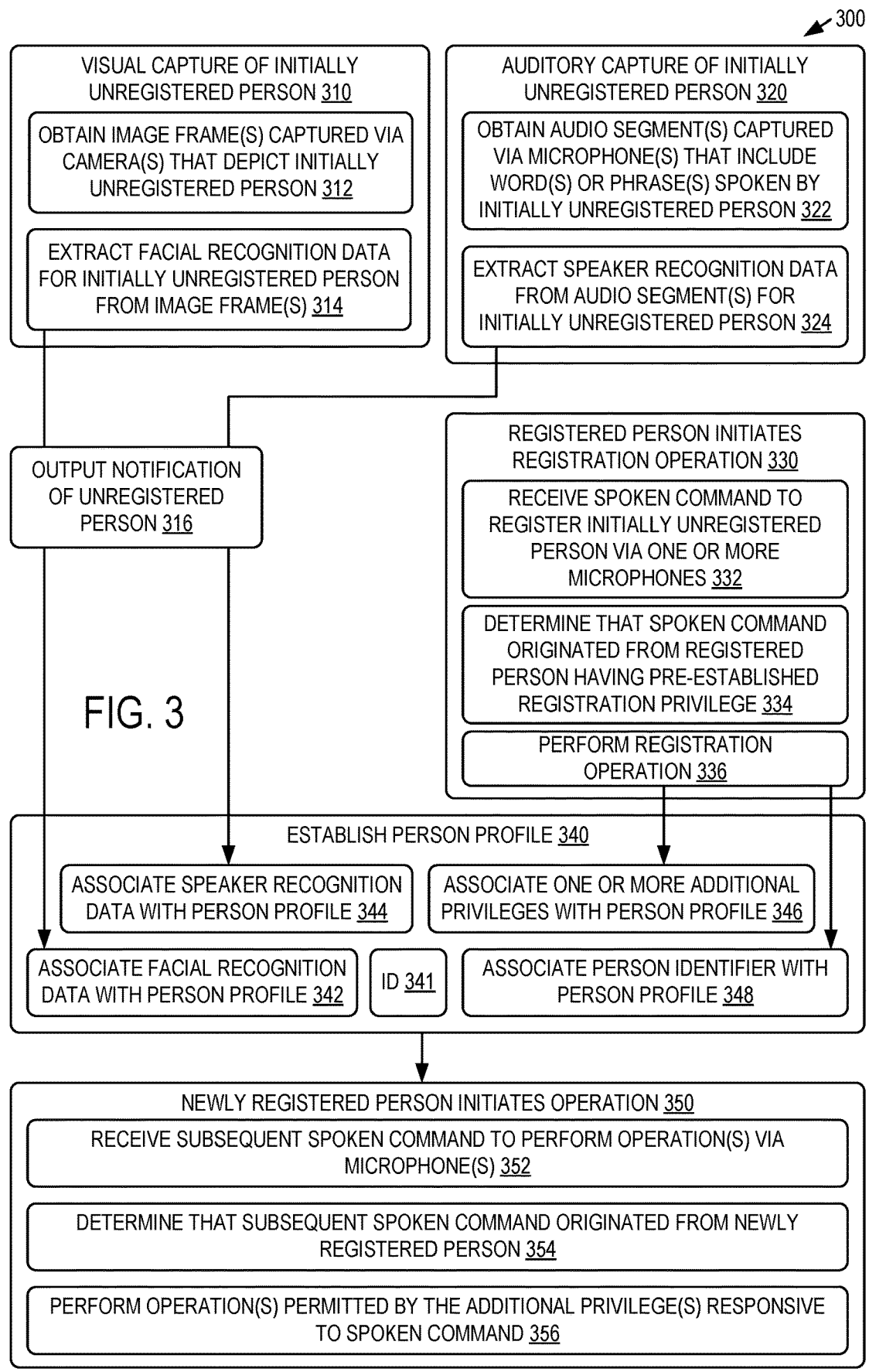
FIG. 3 is a flow diagram depicting an example method for registering a person with an intelligent assistant computer.

FIG. 3 is a flow diagram depicting an example method 300 for registering a person with an intelligent assistant computer. Method 300 may be performed by a computing system that includes the intelligent assistant computer, such as the previously described computing systems of FIGS. 1 and 2, for example.

At 310, visual capture of an initially unregistered person may be performed. As described in further detail below, the computing system may compare facial recognition data extracted from image frames of persons observed by the computing system via one or more cameras to a database of previously observed persons to determine if a person is registered or unregistered. If a person cannot be matched to a previously observed person, the computing system may establish a new person profile for that unrecognized person, and identify that person as being initially unregistered.

At 312, the method includes obtaining one or more image frames captured via one or more cameras that depict an initially unregistered person. The one or more image frames may form part of one or more video segments captured via the one or more cameras. These image frames or their video segments may capture the initially unregistered person that is present within a monitored region from multiple camera angles and/or over multiple visits by the initially unregistered person to the monitored region. Therefore, the one or more image frames may depict the initially unregistered person at different points in time that spans moments, minutes, hours, days, or other suitable time period. The one or more image frames or their video segments captured at 312 may include visible light, infrared, and/or depth representations of the monitored region. The one or more image frames or their video segments captured at 312 may be stored in a data storage system in raw and/or processed forms, and may be subsequently retrieved from the data storage system for further processing by the computing system or for subsequent presentation and review by a user.

At 314, the method includes extracting facial recognition data for the initially unregistered person from the one or more image frames. The facial recognition data extracted at 314 may be stored in a data storage system. As an example, the facial recognition data extracted at 314 may be associated with a person profile established for the initially unregistered user at 342. A person may be visually identified by the computing system by comparing the facial recognition data extracted from image frames to a database of previously obtained facial recognition data stored in a data storage system, such as facial recognition data associated with person profiles, for example. This database may be organized by registered and unregistered persons to enable the computing system to distinguish registered persons from unregistered persons. In at least some implementations, upon identifying or otherwise detecting presence of an unregistered person by visual detection, the computing system may output a notification at 316 to a registered person associated with the computing system. This notification may enable the registered person to review image frames depicting the unregistered person, and if desired, to initiate a registration operation for the unregistered person.

At 320, auditory capture of an initially unregistered person may be performed. As described in further detail below, the computing system may compare speaker recognition data extracted from audio segments of persons' speech observed by the computing system via one or more microphones to a database of previously observed speech to determine if a person is registered or unregistered. If a person cannot be matched to a previously observed person, the computing system may establish a new person profile for that unrecognized person, and identify that person as being initially unregistered.

At 322, the method includes obtaining one or more audio segments captured via one or more microphones that include one or more words or phrases spoken by the initially unregistered person. These audio segments may capture the initially unregistered person speaking within a monitored region from multiple microphone locations and/or over multiple visits by the initially unregistered person to the monitored region. Therefore, the one or more audio segments may capture speech originating from the initially unregistered person at different points in time that spans moments, minutes, hours, days, or other suitable time period. The one or more audio segments captured at 312 may be stored in a data storage system in raw and/or processed forms, and may be subsequently retrieved from the data storage system for further processing by the computing system or for subsequent presentation and review by a user.

At 324, the method includes extracting speaker recognition data from the one or more audio segments for the initially unregistered person. The speaker recognition data extracted at 324 may be stored in a data storage system. As an example, the facial recognition data extracted at 324 may be associated with a person profile established for the initially unregistered person at 344. A person may be audibly identified by the computing system by comparing the speaker recognition data extracted from audio segments to a database of previously obtained speaker recognition data stored in a data storage system, such as speaker recognition data associated with person profiles, for example. As previously described with reference to visual detection of persons, this database may be organized by registered and unregistered persons to enable the computing system to distinguish registered persons from unregistered persons.

Upon identifying or otherwise detecting presence of an unregistered person by audible and/or visual detection, the computing system may output a notification at 316 to a registered person associated with the computing system, as previously described with reference to visual detection of persons. This notification may enable the registered person to review audio segments and/or video segments or image frames of the unregistered person's speech or depiction, and if desired, to initiate a registration operation for the unregistered person.

In at least some implementations, speaker recognition data may be obtained for a person by observing a speaking activity by that person within one or more video segments captured via one or more cameras. As an example, a speaking activity of an initially unregistered person may be identified within the one or more video segments. One or more audio segments, captured via one or more microphones, that are time-matched to the one or more video segments may be obtained by the computing system. Speaker recognition data for the initially unregistered person may be extracted from the one or more audio segments based on one or more spoken words or phrases that correspond to the speaking activity of the initially unregistered person depicted in the one or more video segments.

At 330, registration of the initially unregistered person is initiated by a registered person. At 332, the method includes receiving a spoken command to register the initially unregistered person via one or more microphones. A spoken command to register a person may take various forms, may vary with implementation, and may be user defined through user settings. The previous example of FIG. 1 in which the registered person 120 speaks aloud the phrase "Hey Computer, this is my friend Tom" is a non-limiting example of a spoken command that may be used to register an initially unregistered person. One or more operations of the computing system may be initiated or otherwise activated upon detection of one or more keywords or keyphrases that are spoken by a user. For example, the phrase "Hey Computer" may be used as a keyword phrase to initiate or activate one or more operations of the computing system, such as listening for one or more additional keywords or keyphrases that further indicate one or more additional operations to be performed. In at least some examples, the term "register" or other suitable keyword or keyphrase may be required or otherwise relied upon by the computing system to initiate a registration operation. In yet another example, the computing system may output a query (e.g., visual and/or audible) to the registered person as to whether an unregistered person is to be registered. In response to such a query, the spoken command may take the form of an affirmation, such as "yes" or "ok". Accordingly, a spoken command may take the form of an individual word, individual phoneme, or set of phonemes in at least some implementations.

While a spoken command is described in this example, it will be understood that other suitable commands (i.e., non-spoken and/or non-audible commands) may be received using other forms of user input to initiate registration of a person. For example, a user input indicating a command may be received via a hardware-based user interface such as a touch-screen, a keyboard or keypad, a computer mouse or other pointing device, or other suitable user input device.

At 334, the method includes determining that the spoken command or other suitable command originated from a registered person having a pre-established registration privilege. The pre-established registration privilege may be retrieved or otherwise referenced from a person profile for the registered person stored in a data storage system. The registered person may be identified by one or more of the visual, auditory, or other suitable techniques described in further detail herein. Additionally or alternatively, the registered person may be identified based on context without relying on auditory or visual detection of the registered person. For example, a registered user may provide a non-spoken command via a hardware-based user interface in which the registered person previously logged into the computing system with user credentials (e.g., username and/or password) via the hardware-based user interface.

At 336, the method includes performing a registration operation to register the initially unregistered person as a newly registered person. Registering may be performed at 336 upon determining that the spoken command or other suitable command originated from the registered person having the pre-established registration privilege. The registration privilege associated with a particular person denotes that the person is permitted to register other persons with respect to the computing system. In at least some implementations, a person profile may be established at 340 for an initially unregistered person in response to initiation of the registration operation. However, as previously described with regards to visual and auditory capture of the initially unregistered person at 310 and 320, image data and/or audio data may be associated with a person profile established for the person prior to initiating the registration operation. In this implementation, a person profile may be established upon identification of a new person by the computing system, either by visual or auditory identification and comparison to previously observed persons. A person profile may be established by assigning or associating a profile identifier 341 (e.g., a unique identifier within a particular domain of identifiers) with the person profile to enable that person profile to be distinguished from other person profiles.

Registration may be performed by associating, at 346, one or more additional privileges with respect to the computing system with a person profile for the newly registered person. Depending on implementation, image data including the facial recognition data and/or audio data including the speaker recognition data may be associated with the additional privileges in the person profile at the time of registration, before registration is initiated (e.g., if previously acquired for the then initially unregistered person), or after registration (e.g., when acquired) as will be described in further detail below.

In at least some implementations, some or all of the image frames obtained at 312 may be captured after receiving the spoken command to register the initially unregistered person. As an example, the initially unregistered person may be directed to position its face within a field of view of the one or more cameras to capture the one or more image frames for facial recognition and extracting facial recognition data. Additionally or alternatively, some or all of the one or more audio segments obtained at 322 may be captured after receiving the spoken command to register the initially unregistered person. As an example, the initially unregistered person may be directed to speak one or more words or phrases within range of one or more microphones of the computing system to capture the one or more audio segments for speaker recognition and extracting speaker recognition data.

Directing the initially unregistered person for image or audio capture may include one or more of outputting an audible direction via an audio speaker and/or outputting a visual direction via a graphical display device. The initially unregistered person may be directed by the computing system responsive to or at later time after receiving the spoken command from the registered person to register the initially unregistered person. For example, referring again to FIG. 1, one or more image frames of person 122 (i.e., "Tom") that are captured by a camera (e.g., of computing device 110 or camera 118) may be presented on graphical display device 112 to enable person 122 to position his face within the field of view of the camera. The computing system may provide feedback to the person by outputting a visual and/or audible prompt for the person move closer/further away, up/down, right/left, or to speak louder, to repeat a word or phrase, etc.

In at least some implementations, the spoken command to register the initially unregistered person may be received after some or all of the one or more image frames depicting the initially unregistered person are captured via the one or more cameras. In these implementations, the one or more image frames may be stored in a data storage device prior to receiving the spoken command to register the initially registered person. The one or more image frames may be retrieved from the data storage system, and presented via a graphical display device for review by the registered person. For example, referring again to FIG. 1, one or more image frames of person 122 (i.e., "Tom") may be captured by a camera (e.g., of computing device 110 or camera 118) prior to person 120 providing the spoken command to register person 122.

In at least some implementations, the spoken command to register the initially unregistered person may be received after some or all of the one or more audio segments containing spoken words or phrases of the initially unregistered person are captured via the one or more microphones. In these implementations, the one or more audio segments may be stored in a data storage device prior to receiving the spoken command to register the initially registered person. The one or more audio segments may be retrieved from the data storage system, and presented via an audio speaker for review by the registered person. For example, referring again to FIG. 1, an audio segment containing a spoken word or phrase of second person 122 may be output via audio speakers 114 and 116 for review by person 120 prior to person 120 providing the spoken command to register person 122.

The one or more image frames and/or audio segments of the initially unregistered person may be presented after the initially unregistered person leaves a field of view of the one or more cameras, or after the unregistered person leaves the region monitored by the computing system. For example, the registration process may be initiated by a registered person following presentation of image frames and/or audio segments of the initially unregistered person moments, minutes, hours, days, or other suitable time period after the initially unregistered person leaves the monitored region.

The spoken command may be received during or after presentation of the one or more image frames and/or audio segments of the initially unregistered person. For example, referring again to FIG. 1, person 120 may provide the spoken command while viewing an image frame of second person 122 upon graphical display device 112, whether or not second person 122 is still present at region 130. In at least some implementations, the one or more image frames may be presented responsive to another command initiated by the registered person, such as another command, spoken or other, that directs the computing system to present imagery or audio of unregistered persons that was captured by the computing system.

At 350, the newly registered person initiates an operation. In this example, the operation is initiated by a spoken command. For example, at 352, the method includes receiving a subsequent spoken command to perform one or more operations via one or more microphones. At 354, the method includes determining that the subsequent spoken command originated from the newly registered person having the one or more additional privileges based on the speaker recognition data. As an example, the computing system may retrieve or otherwise reference speaker recognition data associated with some or all of the person profiles to identify a particular person from which the spoken command originated.

At 356, the method includes performing an operation of the one or more operations that is permitted by the one or more additional privileges responsive to the spoken command. Each privilege may permit one or more associated operations to be performed by the intelligent assistant service responsive to a command originating from a person associated with that privilege. As an example, the one or more additional privileges associated with the newly registered person may permit one or more operations, not previously permitted prior to registration, to be performed by the intelligent assistant service responsive to a spoken command originating from the newly registered person. In at least some implementations, unregistered users or unidentified persons may have an initial set of privileges (i.e., a base privilege set). Following registration, the newly registered user may provide a spoken command to, for example, turn on the lights in a room serviced by the computing system. Responsive to identifying the spoken command as originating from the newly registered person associated with a privilege permitting the lights to be turned on, the computing system may output a control signal to turn on the lights in the room. In this example, the newly registered person prior to registration (as an initially unregistered person) might not have the privilege permitting the lights to be turned on by the computing system within the base privilege set initially assigned to all unregistered users or unidentified persons. As another example, a privilege identifier may indicate whether the newly registered person is permitted to register other initially unregistered persons (i.e., a registration privilege). In this example, the newly registered person prior to registration might not have the registration privilege within the base privilege set.

The spoken command received at 332 may include or form part of a spoken phrase that originated from the registered person that further includes a person identifier and/or a privileges identifier for the newly registered person. A person identifier may take the form of a person's name or nickname to be assigned to the person being registered. At 348, the method may further includes associating the person identifier with the person profile for the newly registered person. At 346, the method may further includes associating the privileges identifier with the person profile for the newly registered person.

A privileges identifier may be used to identify the one or more additional privileges associated with the person profile for the person being registered. The computing system may support one, two, or more privilege identifiers, each having its own respective set of privileges. A privileges identifier may take various forms depending on implementation, and may be user-defined within user settings. As an example, a privileges identifier may take the form of a relationship-based keyword or keyphrase, such as "friend", "family", "guest", "colleague", "wife", "husband", "child", etc. with each keyword or keyphrase referring to its own respective set of privileges. As another example, a privileges identifier may take the form of a hierarchical set of keyword or keyphrase values, such as "level 1", "level 2", "level 3", etc. with each keyword or keyphrase again referring to its own respective set of privileges.

A person may remain a registered person for a predefined duration following their registration with the computing system, after which the registration optionally may be terminated by the computing system. As an example, the predefined duration may be minutes, hours, days, years, or indefinite. Additionally or alternatively, the predefined duration may be based on continual presence of the registered person within the monitored region of the computing system. As an example, a person may remain registered until that person leaves the premises or if that person leaves the premises but does not return to the monitored region within a threshold period of time of leaving. The predefined duration and/or threshold period of time may be set or otherwise defined by a user setting maintained by the computing system. The user setting for a newly registered person may be available to another registered person that is associated with the registration privilege or other type of privilege. The user setting may be available to any registered person with respect to the predefined duration associated with their own registration, thereby enabling that person to terminate their registration with the computing system. Upon termination of registration for a person, the person profile and associated data for that person may be deleted, made inaccessible, overwritten, or made available to be overwritten by new data. In this way, a lifespan of information associated with a person's registration may be controlled and its further dissemination or use may be limited.

Figure 4:
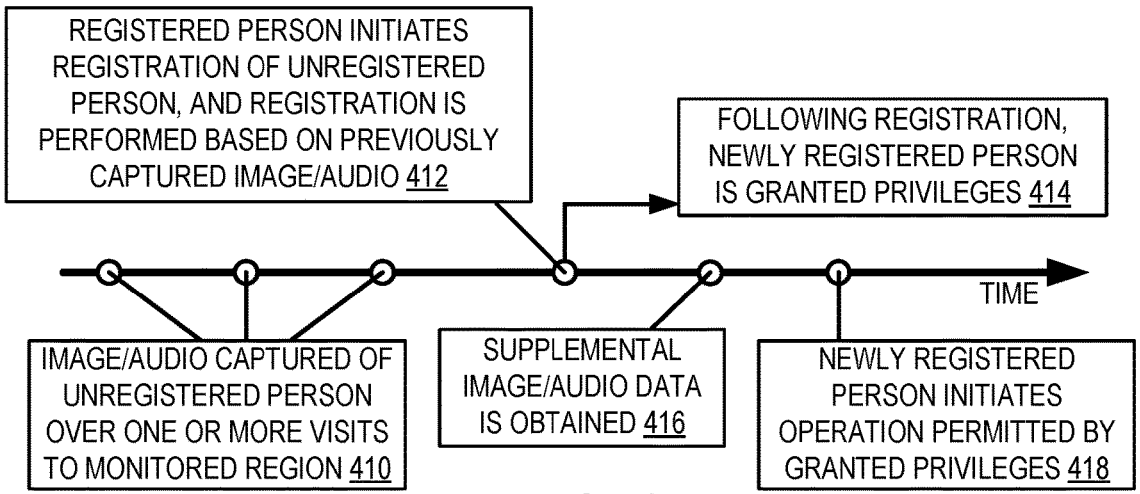
FIG. 4 depicts a timeline of an example implementation in which registration of an initially unregistered person is initiated and performed after image and/or audio data of that initially unregistered person is captured by an intelligent assistant computing system.

FIG. 4 depicts a timeline of an example implementation in which registration of an initially unregistered person is initiated and performed after image and/or audio data of that initially unregistered person is captured by an intelligent assistant computing system. At 410, image data and/or audio data is captured by the computing system for an unregistered person over one or more visits to the monitored region. For example, the computing system may perform the previously described operations of FIG. 3 associated with visual capture of the initially unregistered person at 310 to obtain image data and/or auditory capture of the initially registered person at 320 to obtain audio data. Image data may include one or more images, one or more video segments, and/or facial recognition data derived therefrom. Audio data may include one or more audio segments and/or speaker recognition data derived therefrom.

At 412, a registered person (e.g., with a registration privilege) initiates registration of the initially unregistered person, and registration is performed by the computing system based on the previously captured image data and/or audio data. For example, the computing system may perform the previously described operations of FIG. 3 associated with the registration operation at 330 and the user profile at 340. Following registration, the newly registered person is granted one or more additional privileges as indicated at 414. Also following registration, the computing system may optionally obtain supplemental image data and/or audio data for the newly registered person as indicated at 416. At 418, the newly registered person initiates an operation that is permitted by the privileges granted to the person.

Supplemental image data obtained after registration may include one or more image frames of the newly registered person that are in addition to image frames captured prior to registration and/or one or more audio segments captured prior to registration in the absence of any previously captured image frames of the person being registered. For example, auditory detection of speech by a newly registered person may be used to visually identify the speaker, and capture image frames and facial recognition data derived therefrom for that person after registration. Supplemental image data may be used to extract facial recognition data and/or further refine or update the facial recognition data for a person. In at least some implementations, supplemental image data may include images or video segments obtained from third-party sources, such as social media services, photo or video libraries, etc. that are accessible to the computing system over a communications network.

Supplemental audio data obtained after registration may include one or more audio segments capturing speech of the newly registered person that are in addition to audio segments captured prior to registration and/or image frames captured prior to registration in the absence of any previously captured audio segments of the person being registered. For example, visual detection of a speaking activity by a newly registered person may be used to visually identify and capture audio segments and speaker recognition data derived therefrom for that person after registration. Supplemental audio data may be used to extract speaker recognition data and/or further refine or update the speaker recognition data for a person. In at least some implementations, supplemental audio data may include audio segments (individually as well as those associated with video segments) obtained from third-party sources, such as social media services, photo and video libraries, etc. that are accessible to the computing system over a communications network.

Figure 5:
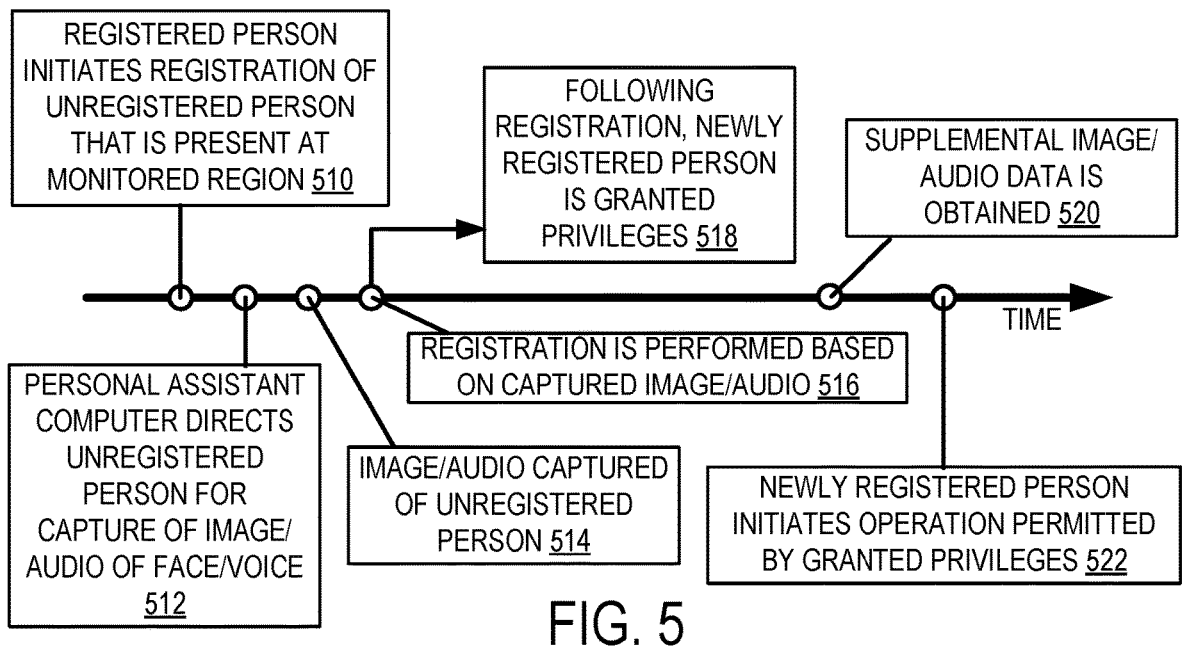
FIG. 5 depicts a timeline of another example implementation in which registration of an initially unregistered person is initiated and image and/or audio data of that initially unregistered person is captured by an intelligent assistant computing system as part of the registration operation.

FIG. 5 depicts a timeline of another example implementation in which registration of an initially unregistered person is initiated and image and/or audio data of that initially unregistered person is captured by an intelligent assistant computing system as part of the registration operation. At 510, a registered person (e.g., with a registration privilege) initiates registration of an initially unregistered person. At 512, the computing system optionally directs the initially unregistered person with regards to capture of one or more image frames of the person's face for facial recognition and/or one or more audio segments of the person's voice or speech for speaker recognition. At 514, image frames and/or audio segments are captured and facial recognition data and/or speaker recognition data is obtained therefrom. At 516, the computing system performs the registration operation based on the captured image frames and/or audio segments of the person being registered. Following registration, the newly registered person is granted one or more privileges as indicated at 518. At 520, supplemental image data and/or supplemental audio data is optionally obtained to extract, refine, or update facial recognition data and/or speaker recognition data. At 522, the newly registered person initiates an operation that is permitted by the privileges granted to the person.

While the timelines of FIGS. 4 and 5 depict different implementations, it will be understood that these implementations may be combined into a workflow that includes the capture of image data and/or audio data of a person prior to their registration, the capture of image data and/or audio data as part of the registration operation for that person, and optionally the capture of supplemental image data and/or audio data following registration of that person. With each new image frame or audio segment that is captured, the facial recognition data and/or speaker recognition data may be refined and improved to provide more accurate detection and identification of that person.

Referring again to FIG. 2, additional descriptions of the components of intelligent assistant computing system 200 will now be provided. In some examples, voice listener 230 may receive audio data from the surrounding environment. In some examples, such as in computing device 110 of FIG. 1, the voice listener 230 may comprise a software module that is embodied in a standalone device that comprises one or more microphones. In other examples, the voice listener 230 software module may be stored in memory of a computing device that is located remotely from the user's environment, such as in a cloud-based service. In some examples, additional data from one or more other sensors may be received and utilized by the voice listener 230 in performing its functions that are described in more detail below. The voice listener 230 may comprise speech recognition functionality that translates audio data of spoken utterances into text. As described in more detail below, the voice listener 230 also may assign a confidence value to one or more portions of translated text, such as individual speech components, words, phrases, etc.

Figure 6:
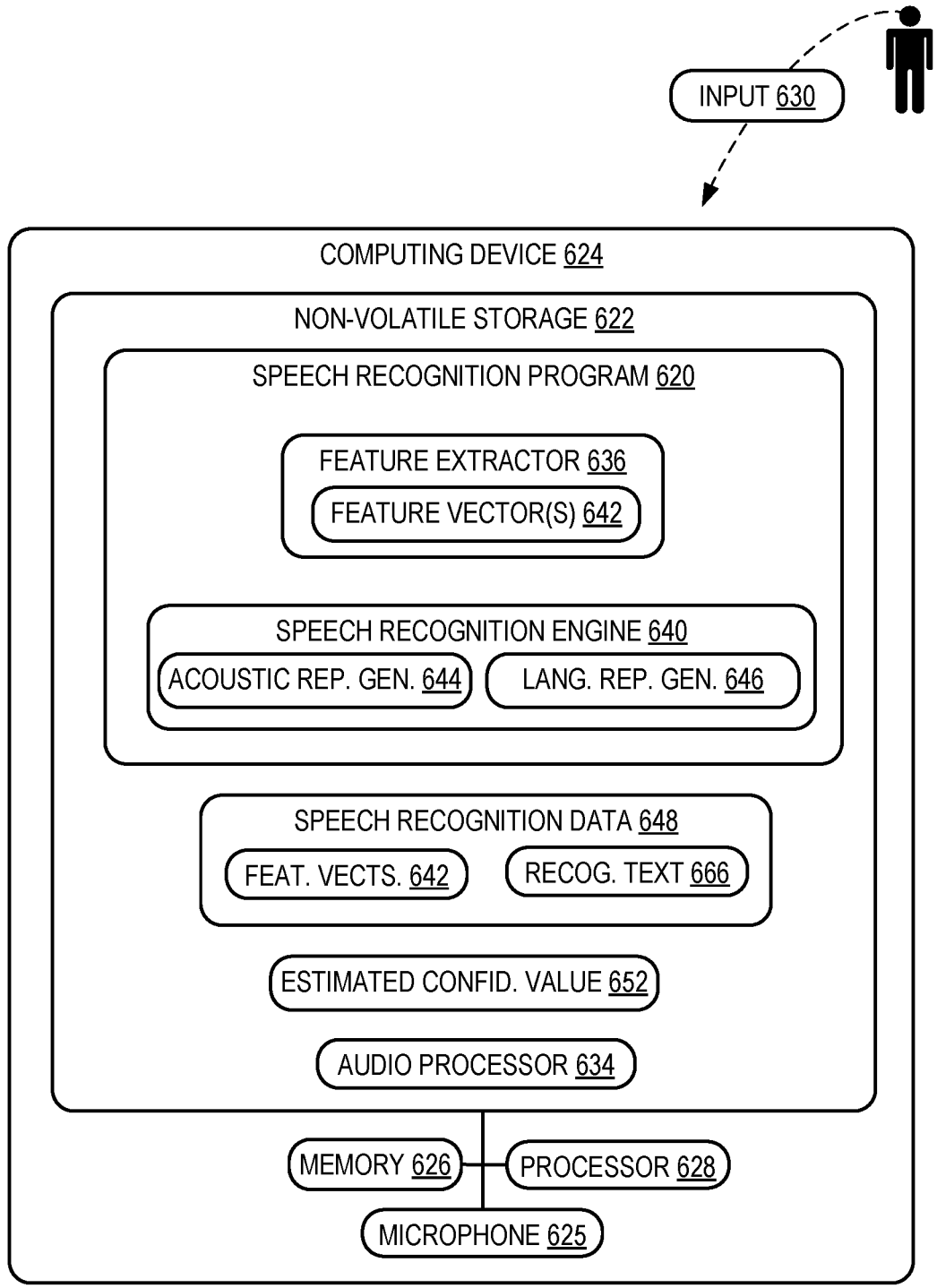
FIG. 6 schematically shows a speech recognition program that may be utilized by a voice listener according to an example of the present disclosure.

With reference now to FIG. 6, in some examples the voice listener 630 may comprise a speech recognition program 620 stored in non-volatile storage 622 of a computing device 624. The speech recognition program 620 may be loaded into memory 626 and executed by a processor 628 of computing device 624 to perform one or more of the methods and processes for speech recognition described in more detail below.

Audio input 630 in the form of natural language speech may be captured by microphone 625 and processed by audio processor 634 to create audio data. Audio data from the audio processor 634 may be transformed by feature extractor 636 into data for processing by a speech recognition engine 640 of the speech recognition program 620. In some examples, feature extractor 636 may identify portions of the audio data over a time interval that contain speech for processing. Feature extractor 636 may extract feature vectors 642 from such portions of the data, with a feature vector representing the qualities of a spoken utterance within the time interval of a given portion. A matrix of multiple feature vectors 642 may be provided to the speech recognition engine 640 for further processing.

Feature extractor 636 may utilize any suitable dimensionality reduction techniques to process the audio data and generate feature vectors 642. Example techniques include using mel-frequency cepstral coefficients (MFCCs), linear discriminant analysis, deep neural network techniques, etc.

The speech recognition engine 640 may compare the feature vectors 642 generated by feature extractor 636 with acoustic models for speech sounds (e.g., speech components). Examples of speech components may include phonemes, phones, diphones, triphones, etc. In some examples, the speech recognition engine 640 may comprise an acoustic representation generator 644 (e.g., acoustic modeler) that evaluates the similarity of a spoken utterance represented by one or more feature vectors 642 to acoustic models of language sounds. The acoustic models may comprise data that matches pronunciations of speech components, such as phonemes, to particular words and/or phrases.

The speech recognition engine 640 also may compare the feature vectors and other audio data with sequences of sounds to identify words and/or phrases that match the spoken sounds of the audio data. The speech recognition program 620 may comprise a language representation generator 646 (e.g., language modeler) that may utilize language models to evaluate the likelihood that a particular word would be included in a phrase (which in some cases may comprise a sentence) at a particular location. For purposes of the present disclosure, a phrase may include two or more words that may or may not be considered a complete sentence.

In some examples, the speech recognition engine 640 may utilize Hidden Markov models (HMMs) to match feature vectors 642 with phonemes and/or other speech components. An HMM outputs sequences of n-dimensional vectors, where n is an integer such as 10. Sequences may be generated at a given frequency, such as one sequence every 10 milliseconds.

Each state of an HMM may comprise a statistical distribution that is a mixture of diagonal covariance Gaussians, which may indicate a likelihood for each observed vector. Each phoneme or word may have a different output distribution. Individual HMMs for separate phonemes and words may be combined to create an HMM for a sequence of phonemes or words.

Context dependency for phonemes may be provided by different states of an HMM. Such context-dependent HMM states may be associated with a model, such as a Gaussian mixture model (GMM). In some examples, transitions between states may be assigned probabilities that correspond to a likelihood that a current state may be reached from a previous state. Different paths between states of the HMM may represent inputted sounds, with the different paths representing multiple possible text matches for the same sound.

Using the feature extractor 636 and speech recognition engine 640, the speech recognition program 620 may process feature vectors 642 and other speech recognition data 648 to generate recognized text 666. In other examples, any suitable techniques for matching feature vectors 642 to phonemes and/or other speech components may be utilized.

In some examples, the speech recognition program 620 may determine estimated confidence values 652 for one or more portions of the speech recognition data 648, such as individual speech components, words and phrases. An estimated confidence value 652 may define a statistical likelihood that the corresponding recognized text is accurate. As described in more detail below, the parser 240 of intelligent assistant computing system 200 may utilize such confidence values 652 in processing recognized text and determining a user's intent.

In different examples, confidence values 652 may be determined by utilizing one or more statistical analysis methods, machine learning techniques, empirically-derived data, and combinations of the foregoing. In some examples, the speech recognition program 620 may utilize one or more probabilistic models to analyze portions of the speech recognition data 648, one or more results extracted from the speech recognition analysis pipeline, and/or estimated confidence values 652 associated with such portions. For example, GMMs may be utilized to analyze portions of the speech recognition data 648 and corresponding results. It will be appreciated that any other suitable machine learning techniques, such as various supervised learning and unsupervised learning approaches, may be utilized to analyze the speech recognition data 648.

It will be appreciated that the foregoing descriptions of speech recognition techniques are merely examples, and that any suitable speech recognition technologies and processes may be utilized and are contemplated within the scope of the present disclosure.

With reference again to FIG. 2, in some examples the voice listener 230 may receive context information including associated confidence values from entity tracker 210. As described in more detail below, entity tracker 210 may determine an identity, position, and/or current status of one or more entities within range of one or more sensors, and may output such information to one or more other modules, such as voice listener 230, commitment engine 260, etc. In some examples, entity tracker 210 may interpret and evaluate sensor data received from one or more sensors, and may output context information based on the sensor data. Context information may include the entity tracker's guesses/predictions as to the identity, position, and/or status of one or more detected entities based on received sensor data. In some examples, the guesses/predictions may additionally include a confidence value defining the statistical likelihood that the information is accurate.

With continued reference to FIG. 2, the voice listener 230 may send recognized text and corresponding confidence values to the parser 240. As described in more detail below, the parser 240 analyzes the text and confidence values to determine an intent of the user in speaking the received utterance. The parser 240 may translate the natural language text received from the voice listener 230 into a machine-executable language that represents a user's intention underlying the natural language.

In some examples, a user's intention may correspond to a command to be executed immediately, such as the utterance "Play song A by artist B" (a "Play music" intent). In some examples, an intent may be characterized as a commitment to execute an action upon the occurrence of a trigger, hereinafter referred to as an "add commitment" intent. For example, the utterance "When Bob gets home remind him to take out the trash" is an add commitment intent. In this example, the trigger is Bob arriving home, and the action is to remind him to take out the trash. Another example of an add commitment intent may be the utterance "When Keith is near the oven, alert me." In this example, the commitment of this add commitment intent comprises a trigger (Keith is near the oven) and an action (alert me) to be executed when the trigger is detected. Additional descriptions and examples of commitments are provided below.

In some examples the parser 240 may utilize a plurality of intent templates that each contain a plurality of slots that may be filled with words or terms received from the voice listener 230, or with words or terms that are based on other words received from the voice listener. In some examples where one or more slots are not filled, the parser 240 may fill these slots by examining a semantic meaning of one or more other words. For example, the intelligent assistant computing system 200 may tell a user, "You have 15 emails" The user may respond with an utterance, "OK, I'll go through them when I'm in the car." In response to the user's utterance, the parser 240 may fill a "commitment type" slot with the type "reminder", even though the word "reminder" itself was not in the user's utterance.

Taken together, the plurality of slots of an intent template define or otherwise characterize the intent of the user in speaking an utterance. In various different examples, the slots may comprise an action slot, a trigger slot, a commitment slot, a subject slot, a content slot, an identity slot, and various other types of slots. In some examples, each slot may embody one of three states: (1) missing information, (2) information present with unresolved ambiguity, and (3) information present with any ambiguity resolved.

In some examples, one or more slots may be optional slots that need not be filled. For example, in one scenario two slots may represent optional information, while in another scenario the same two slots may represent required information. For example, the utterance "Play music" may be understood as a command that music should be played out of the device being used for this conversation. In this manner, the system infers information regarding the user's intention (to play music via the device being used for the conversation) without requiring the user to explicitly state this information. In a different example, the utterance "Whenever it's Eve's birthday, play Happy Birthday" will require the user to specify the device to use, since the play music action is scheduled to be performed some time in the future whenever the specified condition is met.

Figure 7:
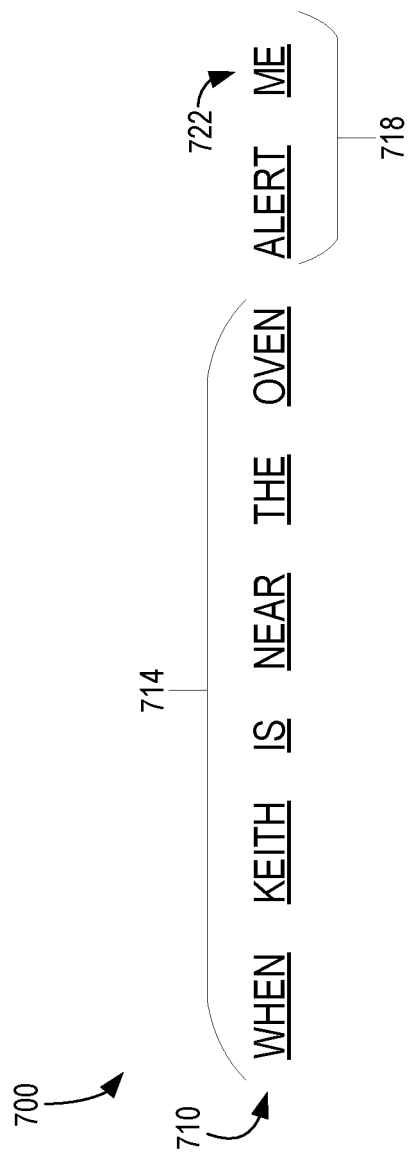
FIG. 7 shows of an intent template according to an example of the present disclosure.

One example of an intent template is a commitment intent template that corresponds to an add commitment intent. With reference now to FIG. 7, one example of a commitment intent template 700 is illustrated. In this example, the parser may receive text phrase 710 from the voice listener 230 that reads "When Keith is near the oven alert me." The phrase "When Keith is near the oven" may be identified as a trigger 714. The phrase "alert me" may be identified as an action 718 that is to be carried out when the trigger is detected. As described in more detail below, in some examples the parser 240 may translate this text phrase 710 into machine-executable language that is passed to the intent handler 230 for further processing.

As noted above, the parser 240 may receive accuracy confidence values from the voice listener 230 that denote a likelihood that corresponding text is accurate. In some examples and as described in more detail below, the intent handler 250 also may receive entity confidence values that are associated with entity information. In some examples, such entity confidence values and other context information may be received via the entity tracker 210.

In the present example, the word "me" in phrase 710 fills a subject slot 722. In this example, the subject slot 722 corresponds to the person or other entity to be alerted when the trigger is detected. The word "me" may be received by the parser 240 with context information that associates this word to a particular person named Joe, and with an entity confidence value, such as 90%, that denotes a level of certainty that "me" is the person "Joe."

In some examples, the intended meaning of one or more words in an intent template may not be readily apparent. For example, in phrase 710 the meaning of the word "near" may be ambiguous, as "near" is a relative term. A variety of contextual factors may influence the intended meaning of "near" and the corresponding distance contemplated in this phrase. For example, where "Keith" is an infant, the intended meaning of "near" may be based on important safety concerns of the user speaking the phrase. Where "Keith" is the husband of the user, the intended meaning of "near" may be influenced less by safety concerns and more by convenience factors, which may lead to an associated distance that is different from the case where "Keith" is an infant. In another example, the distance intended to be conveyed in the phrase "near the oven" is likely different from the distance intended to be conveyed in the phrase "near the Statue of Liberty."

Accordingly, one or more words in an intent template may be ambiguous as passed to the intent handler 250. As described in more detail below, the intent handler 250 may utilize a plurality of techniques to resolve ambiguities and to fill in slots with missing information in an intent template.

In another example, the parser 240 may receive the text phrase "Play music with Fred" from the voice listener 230. In some examples, the phrase "Play music" is often interpreted to mean that a user wants to play digital music files via a media player. However, the use of the phrase "with Fred" following "Play music" is unusual, as people typically would not use this phrasing when their intent is to play music via a media player. The parser 240 may recognize this ambiguity and may generate a list of N-best intent templates that it determines are the statistically most probable intent templates corresponding to the user's actual intent. In some examples, the intent handler 250 may use additional context information to select an intent template from the list of N-best intent templates.

In another example, the text phrase received from the voice listener 230 may be the single word "Play." For example, the word or words spoken by the user after "Play" may have been unintelligible to the voice listener for one or more reasons (such as loud noises in the background). In this example, the parser 240 may predict that the user's intent is to play digital music, but in the corresponding intent template the content slot representing what music to play is empty. In this example, the parser 240 may send a "Play music" intent template to the intent handler 250 for further processing and resolution of this ambiguity, as described in more detail below.

In some examples, the parser 240 may analyze received text to form a decision tree of the user's intent. In some examples, the parser 240 may generate If-Then statements (or rules) from the received text. Each If-Then statement may comprise a corresponding trigger and an action. Whenever the conditions of the trigger are satisfied, the action is performed. The resulting If-Then statements can perform a wide variety of tasks, such as home security ("text me if the motion detector in the back yard is activated"), home automation ("turn on the fireplace when I arrive home"), personal organization ("collect my email receipts for charitable donations into a spreadsheet"), health-related tasks ("remind me to eat protein if I run more than 7 miles"), and many others.

In some examples, triggers and actions may be drawn from a range of channels that may be activated by a user. These channels may represent different entities and services, including devices (such as smart phone operating systems, connected home components such as smart light switches, etc.), knowledge sources (such as entertainment websites, email providers, etc.), and the like. Each channel may expose a set of functions for both the trigger and the action.

For example, If-Then statements may take the form of "IF [Input(s)] are recognized, THEN perform [Action(s)]". For example, the received phrase "When Oz is in the kitchen, tell him to take out the garbage" may be translated to the following If-Then statement: "IF the person Oz is determined to be in the kitchen, THEN broadcast a message to the person Oz to take out the garbage." In some examples, the parser 240 may determine that a user intends to establish a recurring a message or action based on parsing a received utterance. For example, in the phrase "When Oz is in the kitchen, tell him to take out the garbage," the word "when" may be interpreted by the parser 240 to designate that the corresponding action should be performed each time the condition is met (i.e., each time Oz is in the kitchen, tell him to take out the garbage). In another example, in the phrase "If Oz is in the kitchen, tell him to take out the garbage," the word "if" may be interpreted to designate that the corresponding action should be performed one time only (i.e., the next time Oz is in the kitchen, tell him to take out the garbage).

In some examples and as noted above, these If-Then statements may be generated probabilistically. In this manner and for a given string of text, the parser 240 may generate a plurality of N-best candidates of If-Then statements that may correspond to the user's utterance.

In some examples of parsing If-Then rules, the parser 240 may utilize a meaning representation that comprises an abstract syntax tree (AST) in a very simple language. For example, each root node may expand into a "trigger" and "action" pair. These nodes in turn expand into a set of supported triggers and actions. These trees may be modeled as a nearly context-free grammar that generates If-Then tasks.

In some examples, the parser 240 may use an ensemble of two techniques to generate If-Then statements and/or derive an intent from the text received from the voice listener 230: (1) a recurrent neural network (RNN) architecture in the form of a long short-term memory (LSTM) network, and (2) a logistic regression model. In some examples, a graph long short term memory (graph LSTM) neural network may be utilized to extract from received text semantic meanings and relationships between words that are inherent to natural language. For example, text may be parsed using a graph LSTM neural network to extract cross-sentence n-ary relationships using several graph LSTM units arranged according to the syntactic relations of terms in the segment of text. These syntactic relationships between words may be tracked in the graph LSTM neural network to allow artificial intelligence and machine learning techniques to identify entities and their context within the text and from the grammatical structure in which they exist. For example, context that identifies the nouns to which pronouns refer, the adverbs that modify given verbs, the prepositional phrases that affect a given word, etc., may be incorporated into the various words to enable more accurate searches of the contents of natural language documents.

In some examples, the parser 240 may receive and process text to graph nodes (e.g., words, phrases, characters, etc.) and edges (e.g., dependency links between nodes) in individual phrases and across boundaries of phrases. In various examples, the graphing may include identifying one or more links (e.g., syntactic, semantic, co-reference, discourse, etc.) between nodes in the text. The links can include intra-phrase and inter-phrase links between nodes. For example, a link can represent a relationship between the root of one phrase and the root of an adjacent phrase. For another example, a link can represent a relationship between two words in a phrase, such as the modifier "Annie's" to the word "lunch."

As described above, in some examples the parser 240 passes an intent template to the intent handler 250 for further processing. The intent handler 250 comprises a multi-step pipeline that may resolve ambiguous information and/or information that is missing from an intent template. As described in more detail below, the intent handler 250 may utilize a plurality of techniques to resolve ambiguities and fill in missing information slots with respect to an intent template. In some examples, the intent handler 250 may utilize domain-specific information and domain-specific reasoning to resolve ambiguities, complete missing information, and otherwise clarify an intent template to more closely correspond to the actual intent of the user.

In some examples, the intent handler 250 may glean knowledge regarding the user's intent by analyzing prior utterances of the user in a conversation history, and may utilize such insights to resolve ambiguities and add missing information to an intent template. Once the intent handler 250 has sufficiently clarified ambiguities and completed missing information, a corresponding commitment may be generated and passed to the commitment engine 260 for execution.

The intent handler 250 may be configured to process multiple intent templates that may comprise a conversation.

For purposes of the present disclosure and as described in more detail below, a conversation may comprise a plurality of information and other data related to one or more exchanges between the user and the intelligent assistant computing system 200. In different examples, such information and data may comprise words and/or phrases spoken by a user, queries presented to the user by the intelligent assistant computing system 200, sensor data received from one or more sensors, context information such as person and/or identity information, etc.

As described in the use case examples provided below, the intent handler 250 may comprise a plurality of resolvers that translate intent templates and their associated data received from the parser 240 into internal data references. To address slots that comprise missing and/or unresolved information in an intent template, the intent handler 250 may utilize the plurality or resolvers in a multi-stage process. In some examples, each of the resolvers may be specifically programmed to handle issues associated with a particular intent template that may be received from the parser 240.

Examples of resolvers may include lookup resolvers that translate proper names, aliases, and other identifiers into internal representation data (for example, "Bob" is translated to an internal representation of the person "Bob", such as Bob's contact information). Examples of resolvers may include anaphoric resolvers that address expressions having an interpretation that depends upon an antecedent or postcedent expression in context (for example, "she" is translated to a slot representing "a personal identity of the pronoun 'she'"), and deixis resolvers that address words and phrases, such as "here" or "there", that cannot be fully understood without additional contextual information (for example, "there" may translated to a slot representing "where is there?"). In other examples, many other forms and types of resolvers may be utilized.

Figure 8:
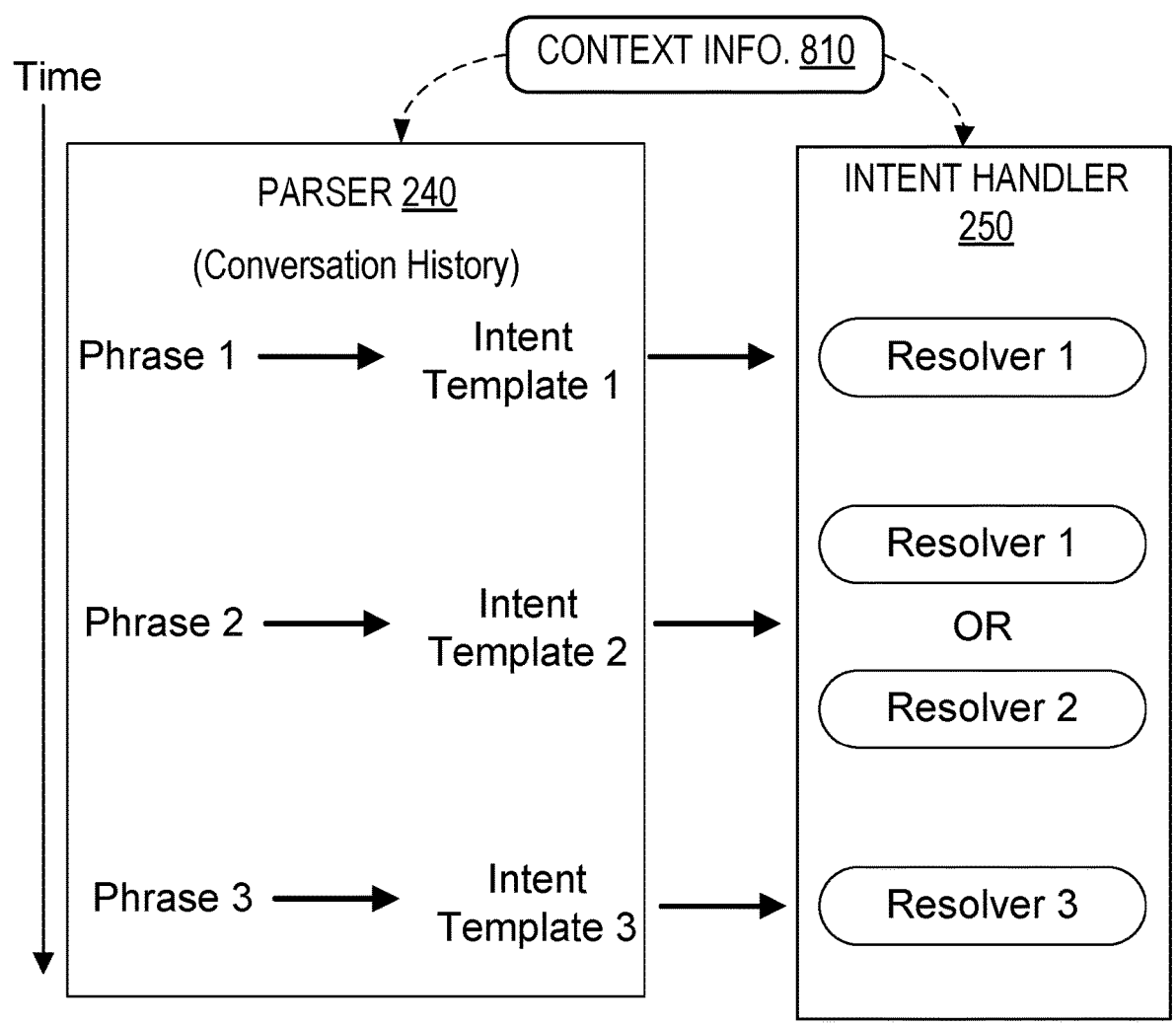
FIG. 8 schematically shows a parser and an intent handler processing a portion of a conversation according to an example of the present disclosure.

With reference now to FIG. 8, one example of the parser 240 and intent handler 250 processing a portion of a conversation is schematically illustrated. In this example, a first phrase 1 is parsed by the parser 240 into an intent template 1. The parser 240 provides intent template 1 to the intent handler 250, which utilizes a first resolver 1 to resolve ambiguities and/or missing information in this intent template. A second intent template 2 corresponding to a second phrase 2 is received from the parser 240. As described in more detail below, the intent handler 250 may analyze the intent template 2 along with context information 810 to determine whether to utilize first resolver 1 or second resolver 2 to resolve the intent template 2. A third intent template 3 based on a third parsed phrase 3 may then be received by the intent handler 250. The intent handler 250 may utilize a third resolver 3 to resolve intent template 3. Additional details and use case examples of analyzing intent templates with resolvers are provided below.

In some examples the intent handler 250 may determine whether two or more intent templates should be fused or merged together to continue with an existing conversation path. If the intent handler 250 determines that the two or more intent templates should be fused together, then the intent handler may fuse the data associated with the two or more intent templates and continue following the existing conversation path with the fused data. If the intent handler 250 determines that the two or more intent templates should not be fused together, then a new topic may be started using the most recently received intent template.

As described in more detail below, where a slot of an intent template has missing information, the intent handler 250 may perform data gathering operations (such as to ask the user to clarify or provide information, or try to gather the information in another way) in order to populate information in the slot. Once each slot contains information, the intent handler 250 may determine if the information in each slot is unambiguous. For information identified as ambiguous, the intent handler 250 may apply one or more of a variety of techniques to resolve the ambiguity.

With reference again to FIG. 2, in some examples the intent handler 250 may comprise a mapper 252 that maps one or more system goals to a corresponding user intent(s). Examples of system goals may include clarifying ambiguities, acquiring additional information from a user, etc. In some examples, mapper 252 may internally rephrase system goals as user intents or goals. For example, mapper 252 may map information the system needs, such as information to resolve an ambiguous intent, to a user intent that the user would have triggered in providing that information. In other words, mapper 252 may map information to the intent that would have been resolved from an utterance that a user would have spoken in order to generate the intent. In some examples, mapper 252 may map a system goal to a word or phrase the user would have said to generate the same outcome.

In some examples, where the system needs information from a user to resolve a user intent, the system may internally cue a state that is equivalent to the state the system would have been in if the user had provided input (such as an utterance) containing all the components of the intent except for the needed information. In other words and in some examples, the system may assume that the user has already provided more input, with that input missing only one or more specific slot(s) corresponding to the needed information. In this manner, the intent handler 250 may continually utilize whatever user input is provided. In some examples, this allows the system to reuse components, such as intent templates. Accordingly and in these examples, by causing the intent handler 250 to assume that user intents (versus system goals) are driving its operation, the system may internally reuse corresponding logic and may understand such user intents with greater depth and richness.

In some examples, the system may have a goal of acquiring information from a user to proceed with deriving a user intent. In a first example, a user may speak two utterances: "Book me a flight to California tomorrow; The flight needs to be to San Francisco." In the first utterance, the user indicates an intent to book a flight, and in the second utterance the user narrows the intent to a flight to San Francisco. In both utterances, a user intent is specified.

In another example, the user speaks a first utterance "Book me a flight tomorrow." The system may respond with a query "Where do you want to fly to?" The user may then respond, "To San Francisco." Upon generating the system query, the mapper 252 may map the intent handler's goal (acquiring information of the user's destination) to a user intent. For example, the mapper 252 may presume that the user is about to provide this information as if it were the user's intent.

In some examples, by configuring the mapper 252 to presume that a user intent is driving its operation, the system may minimize the code to perform these operations and reuse corresponding logic. In this manner, the system may understand such user intents with greater depth and richness. Accordingly, in these examples the system may utilize code for the intent handler 250 and mapper 252 that comprises a user-intent only system, as opposed to utilizing multiple specialized pieces of code to manage all ambiguities and otherwise handle multiple corresponding tasks and discrete situations.

Figure 9:
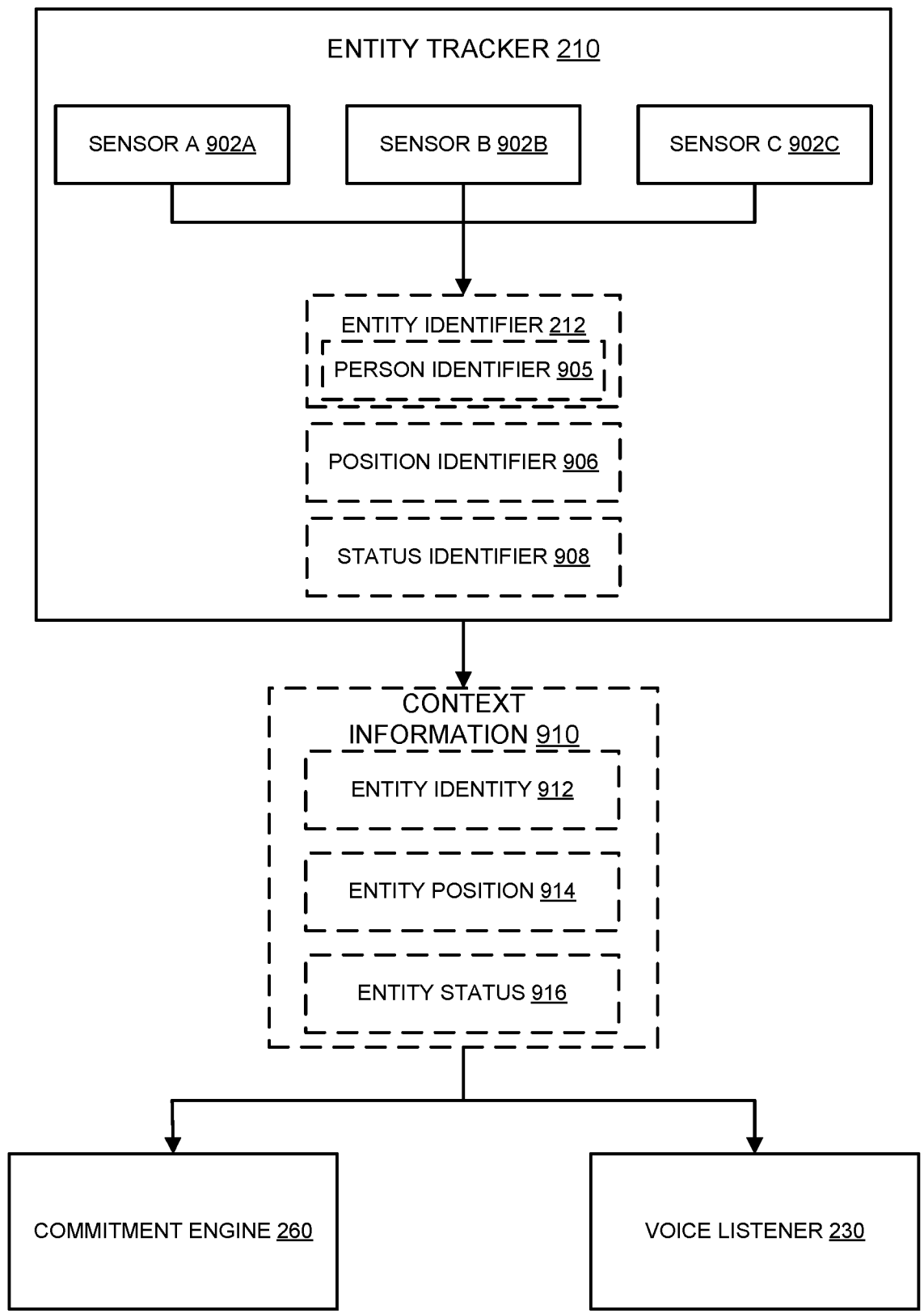
FIG. 9 schematically shows an entity tracker that may determine an identity, position, and/or current status of one or more entities according to examples of the present disclosure.

FIG. 9 schematically illustrates an example entity tracker 210 that may comprise a component of the intelligent assistant computing system 200. Entity tracker 210 may be used to determine an identity, position, and/or current status of one or more entities within range of one or more sensors. Entity tracker 210 may output such information to one or more other modules of intelligent assistant computing system 200, such as the commitment engine 260, voice listener 230, etc.

The word "entity" as used in the context of the entity tracker 210 may refer to people, animals, or other living things, as well as non-living objects. For example, the entity tracker may be configured to identify furniture, appliances, structures, landscape features, vehicles, and/or any other physical object, and determine the position/location and current status of such physical objects. In some cases, the entity tracker 210 may be configured to only identify people and not other living or non-living things. In such cases, the word "entity" may be synonymous with the word "person."

Entity tracker 210 receives sensor data from one or more sensors 222, such as example sensor A 902A, sensor B 902B, and sensor C 902C, though it will be understood that an entity tracker may be used with any number and variety of suitable sensors. As examples, sensors usable with an entity tracker may include cameras (e.g., visible light cameras, UV cameras, IR cameras, depth cameras, thermal cameras), microphones, pressure sensors, thermometers, motion detectors, proximity sensors, accelerometers, global positioning satellite (GPS) receivers, magnetometers, radar systems, lidar systems, environmental monitoring devices (e.g., smoke detectors, carbon monoxide detectors), barometers, health monitoring devices (e.g., electrocardiographs, sphygmomanometers, electroencephalograms), automotive sensors (e.g., speedometers, odometers, tachometers, fuel sensors), and/or any other sensors or devices that collect and/or store information pertaining to the identity, position, and/or current status of one or more people or other entities. In some examples, the entity tracker 210 may occupy a common device housing with one or more of the plurality of sensors 220, and/or the entity tracker and its associated sensors may be distributed across multiple devices configured to communicate via one or more network communications interfaces (e.g., Wi-Fi adapters, Bluetooth interfaces).

As shown in the example of FIG. 9, entity tracker 210 may include an entity identifier 212, a person identifier 905, a position (location) identifier 906, and a status identifier 908. In some examples, the person identifier 905 may be a specialized component of the entity identifier 212 that is particularly optimized for recognizing people, as opposed to other creatures and non-living things. In other cases, the person identifier 905 may operate separately from the entity identifier 212, or the entity tracker 210 may not include a dedicated person identifier.

Depending on the specific implementation, any or all of the functions associated with the entity identifier, person identifier, position identifier, and status identifier may be performed by the individual sensors 902A-902C. Though the present description generally describes the entity tracker 210 as receiving data from sensors, this does not require that the entity identifier 212, as well as other modules of the entity tracker, must be implemented on a single computing device that is separate and distinct from the plurality of sensors associated with the entity tracker. Rather, functions of the entity tracker 210 may be distributed amongst the plurality of sensors. For example, rather than sending raw sensor data to the entity tracker, individual sensors may be configured to attempt to identify entities that they detect, and report this identification to the entity tracker 210, and/or other modules of intelligent assistant computing system 200. In some cases, this identification may include a confidence value.

Each of the entity identifier 212, person identifier 905, position identifier 906, and status identifier 908 is configured to interpret and evaluate sensor data received from the plurality of sensors 220, and to output context information 910 based on the sensor data. Context information 910 may include the entity tracker's guesses/predictions as to an identity, position, and/or status of one or more detected entities based on received sensor data. As will be described in more detail below, each of the entity identifier 212, person identifier 905, position identifier 906, and status identifier 908 may output their predictions/identifications along with a confidence value.

The entity identifier 212 may output an entity identity 912 of a detected entity, and such entity identity may have any suitable degree of specificity. In other words, based on received sensor data, the entity tracker 210 may predict the identity of a given entity, and output such information as entity identity 912. For example, the entity identifier 212 may report that a particular entity is a piece of furniture, a dog, a human male, etc. Additionally, or alternatively, the entity identifier 212 may report that a particular entity is an oven with a particular model number; a pet dog with a specific name and breed; an owner or user of intelligent assistant computing system 200, with the owner/user having a particular name and profile; etc. In some examples, the degree of specificity with which the entity identifier 212 identifies/classifies detected entities may depend on one or more of user preferences and sensor limitations.

When applied to people, the entity tracker 210 may in some cases collect information about individuals whom it is unable to identify by name. For example, the entity identifier 212 may record images of a person's face, and associate these images with recorded audio of the person's voice. Should the person subsequently speak to or otherwise address the intelligent assistant computing system 200, the entity tracker 210 will then have at least some information regarding with whom the intelligent assistant computing system is interacting. In some examples, the intelligent assistant computing system 200 could also prompt the person to state their name, so as to more easily identify the person in the future.

In some examples, the intelligent assistant computing system 200 may utilize a person's identity to customize a user interface for the person. In one example, a user may be identified who has limited visual capabilities. In this example and based on this identification, a display of the intelligent assistant computing system 200 (or other device with which the user is interacting) may be modified to display larger text, or to provide a voice-only interface.

The position identifier 906 may be configured to output an entity position (i.e., location) 914 of a detected entity. In other words, the position identifier 906 may predict the current position of a given entity based on collected sensor data, and output such information as entity position 914. As with the entity identity 912, the entity position 914 may have any suitable level of detail, and this level of detail may vary with user preferences and/or sensor limitations. For example, the position identifier 906 may report that a detected entity has a two-dimensional position defined on a plane such as a floor or wall. Additionally, or alternatively, the reported entity position 914 may comprise a three-dimensional position of a detected entity within a real world, three-dimensional environment. In some examples an entity position 914 may comprise a GPS position, a location within a mapping system, etc.

The reported entity position 914 for a detected entity may correspond to the entity's geometric center, a particular part of the entity that is classified as being important (e.g., the head of a human), a series of boundaries defining the borders of the entity in three-dimensional space, etc. The position identifier 906 may further calculate one or more additional parameters describing the position and/or orientation of a detected entity, such as a pitch, roll, and/or yaw parameter. In other words, the reported position of a detected entity may have any number of degrees-of-freedom, and may include any number of coordinates defining the position of the entity in an environment. In some examples, an entity position 914 of a detected entity may be reported even if the entity tracker 210 is unable to identify the entity, and/or determine the current status of the entity.

Status identifier 908 may be configured to output an entity status 916 of a detected entity. In other words, the entity tracker 210 may be configured to predict the current status of a given entity based on received sensor data, and output such information as entity status 916. "Entity status" can refer to virtually any measurable or classifiable property, activity, or behavior of a given entity. For example, when applied to a person, the entity status of the person can indicate a posture of the person (e.g., standing, sitting, laying down), a speed at which the person is walking/running, a current activity of the person (e.g., sleeping, watching TV, working, playing a game, swimming, talking on the phone), a current mood of the person (e.g., by evaluating the person's facial expression or tone of voice), biological/physiological parameters of the person (e.g., the person's heart rate, respiration rate, oxygen saturation, body temperature, neurological activity), whether the person has any current or upcoming calendar events/appointments, etc. "Entity status" can refer to additional/alternative properties or behaviors when applied to other creatures or non-living objects, such as a current temperature of an oven or kitchen sink, whether a device (e.g., television, lamp, microwave) is powered on, whether a door is open, etc.

In some examples, the status identifier 908 may use sensor data to calculate a variety of different biological/physiological parameters of a human. This may be done in a variety of suitable ways. For example, the entity tracker 210 may be configured to interface with an optical heart rate sensor, a pulse oximeter, a sphygmomanometer, electrocardiograph, etc. Additionally or alternatively, the status identifier 908 may be configured to interpret data from one or more cameras and/or other sensors in an environment, and process the data in order to calculate a human's heart rate, respiration rate, oxygen saturation, etc. For example, the status identifier 908 may be configured to utilize Eulerian magnification and/or similar techniques to amplify miniscule movements or changes captured by the cameras, thereby allowing the status identifier to visualize the flow of blood through a human's circulatory system and calculate associated physiological parameters. Such information can be used, for example, to determine when the person is asleep, working out, in distress, experiencing health problems, etc.

Upon determining one or more of the entity identity 912, entity position 914, and entity status 916, such information may be sent as context information 910 to any of a variety of external modules or devices, where it may be used in a variety of ways. For example, context information 910 may be used by commitment engine 260 to manage commitments and associated messages and notifications. In some examples and as described in more detail below, context information 910 may be used by commitment engine 260 to determine whether a particular message, notification, or commitment should be executed and/or presented to a user. Similarly, context information 910 may be utilized by voice listener 230 when interpreting human speech or activating functions in response to a keyword trigger.

As noted above, in some examples the entity tracker 210 may be implemented in a single computing device. In other examples, one or more functions of the entity tracker 210 may be distributed across multiple computing devices working cooperatively. For example, one or more of the entity identifier 212, person identifier 905, position identifier 906, and status identifier 908 may be implemented on different computing devices, while still collectively comprising an entity tracker configured to perform the functions described herein. As indicated above, any or all of the functions of the entity tracker may be performed by individual sensors 220. Further, in some examples entity tracker 210 may omit one or more of the entity identifier 212, person identifier 905, position identifier 906, and status identifier 908, and/or include one or more additional components not described herein, while still providing context information 910.

Each of entity identity 912, entity position 914, and entity status 916 may take any suitable form. For example, each of the entity identity 912, position 914, and status 916 may take the form of a discrete data packet including a series of values and/or labels describing the information gathered by the entity tracker. Each of the entity identity 912, position 914, and status 916 may additionally include a confidence value defining a statistical likelihood that the information is accurate. For example, if the entity identifier 212 receives sensor data that strongly indicates that a particular entity is a human male named "John Smith," then entity identity 912 may include this information along with a corresponding relatively high confidence value, such as 90% confidence. If the sensor data is more ambiguous, then the confidence value included in entity identity 912 correspondingly may be relatively lower, such as 62%. In some examples, separate predictions may be assigned separate confidence values. For example, the entity identity 912 may indicate with 95% confidence that a particular entity is a human male, and indicate with a 70% confidence that the entity is John Smith. As described in more detail below, such confidence values (or probabilities) may be utilized by a cost function in generating cost calculations for providing messages or other notifications to a user and/or performing action(s).

In some implementations, the entity tracker 210 may be configured to combine or fuse data from multiple sensors in order to output more accurate predictions. As an example, a camera may locate a person in a particular room. Based on the camera data, the entity tracker 210 may identify the person with a confidence value of 70%. However, the entity tracker 210 may additionally receive recorded speech from a microphone. Based on the recorded speech alone, the entity tracker 210 may identify the person with a 60% confidence value. By combining the data from the camera with the data from the microphone, the entity tracker 210 may identify the person with a higher confidence value than would be possible using the data from either sensor alone. For example, the entity tracker may determine that the recorded speech received from the microphone corresponds to lip movements of the person visible to the camera when the speech was received, and thereby conclude with relatively high confidence, such as 92%, that the person visible to the camera is the person speaking. In this manner the entity tracker 210 may combine the confidence values of two or more predictions to identify a person with a combined, higher confidence value.

In some examples, data received from various sensors may be weighted differently depending upon a reliability of the sensor data. This can be especially relevant in situations where multiple sensors are outputting seemingly inconsistent data. In some examples, the reliability of a sensor's data may be based at least in part on the type of data generated by the sensor. For example, in some implementations a reliability of video data may be weighted higher than a reliability of audio data, as the presence of an entity on camera may be a better indicator of its identity, position, and/or status than recorded sounds that are presumed to originate from the entity. It will be appreciated that a reliability of sensor data is a different factor than a confidence value associated with a predicted accuracy of an instance of data. For example, several instances of video data may have different confidence values based on different contextual factors present at each instance. Each of these instances of video data, however, may be associated with a single reliability value for video data in general.

In one example, data from a camera may suggest that a particular person is in a kitchen with a 70% confidence value, such as via face recognition analysis. Data from a microphone may suggest with a 75% confidence value that the same person is in a nearby hallway, such as via voice recognition analysis. Even though the instance of microphone data carries a higher confidence value, the entity tracker 210 may output a prediction that the person is in the kitchen based on a higher reliability of the camera data as compared to a lower reliability of the microphone data. In this manner and in some examples, different reliability values for different sensor data may be used along with confidence values to reconcile conflicting sensor data and determine an identity, position, and/or status of an entity.

Additionally or alternatively, more weight may be given to sensors that have higher precision, more processing power or otherwise greater capabilities. For example, a professional-grade video camera may have a significantly improved lens, image sensor, and digital image processing capabilities as compared to a basic webcam found in a laptop. Accordingly, a higher weight/reliability value may be given to video data received from the professional-grade camera as compared to the webcam, as such data is likely to be more accurate.

With reference now to FIGS. 10-16 additional example implementations of an intelligent assistant computing system in a single computing device and across multiple computing devices are illustrated.

Figure 10:
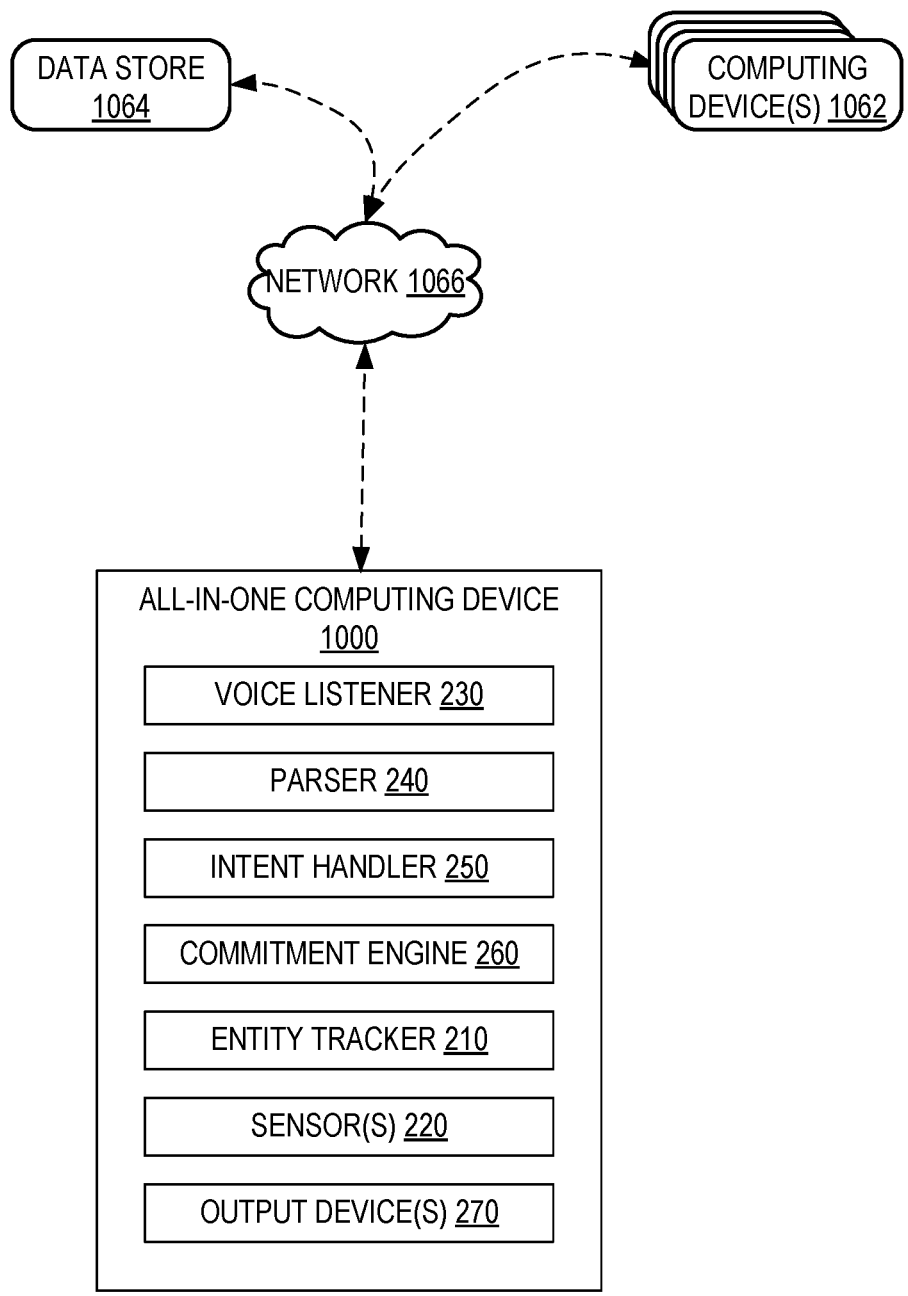
FIG. 10 schematically shows an all-in-one computing device that implements an intelligent assistant computing system according to examples of the present disclosure.

FIG. 10 shows an example of an all-in-one computing device 1000 in which the components implementing intelligent assistant computing system 200 are arranged together in a standalone device. In some examples, all-in-one computing device 1000 may be communicatively coupled to one or more other computing devices 1062 via a network 1066. In some examples, all-in-one computing device 1000 may be communicatively coupled to a data store 1064 that may store a variety of data, such as user profile data. All-in-one computing device 1000 includes at least one sensor 220, voice listener 230, parser 240, intent handler 250, commitment engine 260, entity tracker 210, and at least one output device 270. Sensor(s) 220 include at least one microphone to receive natural language inputs from a user. In some examples one or more other types of sensor(s) 220 also may be included.

As described above, voice listener 230, parser 240, and intent handler 250 work in concert to convert natural language inputs into commitments that are executable by the all-in-one device 1000. The commitment engine 260 stores such commitments in a commitment storage. The entity tracker 210 may provide context information to the commitment engine 260 and/or other modules. At a contextually appropriate time, the commitment engine 260 may execute a commitment and provide output, such as audio signals, to output device(s) 270.

Figure 11:
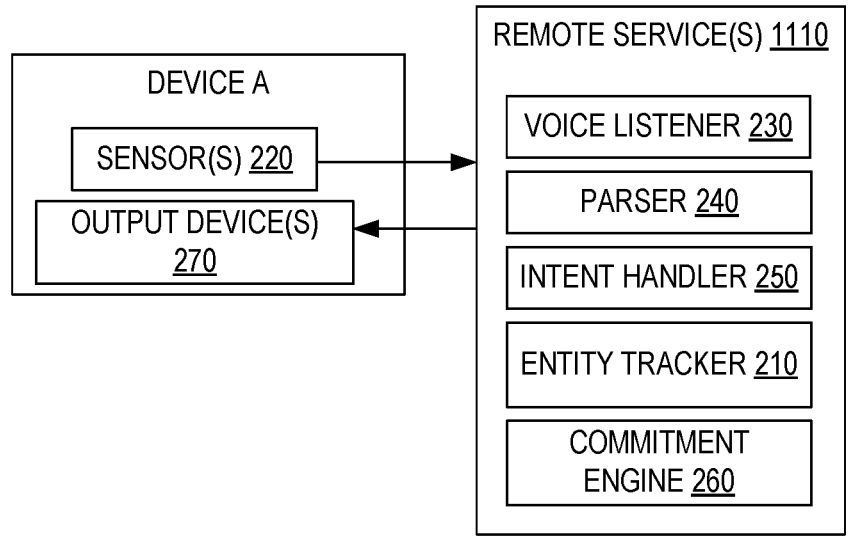
FIG. 11 schematically shows an example implementation in which one or more remote services perform functionality of the intelligent assistant computing system with an individual on-premises computing device according to examples of the present disclosure.

FIG. 11 shows an example implementation in which one or more remote services 1110 perform the natural language processing functionality of intelligent assistant computing system 200. In this example, voice listener 230, parser 240, intent handler 250, entity tracker 210 and commitment engine 260 reside on one or more computing devices, such as one or more servers, that are remotely located from a cloud-supported user device A. Sensor data from one or more sensors 220 of the user device A is provided to remote service(s) 1110 via a network. For example, audio data of a user speaking may be captured by a microphone of user device A and provided to voice listener 230.

As described above, voice listener 230, parser 240, and intent handler 250 cooperate to convert the audio data into commitments that are stored in commitment engine 260. At a contextually appropriate time, the commitment engine 260 may execute a commitment and provide output, such as audio signals, to one or more output device(s) 270 of the user device A.

Figure 12:
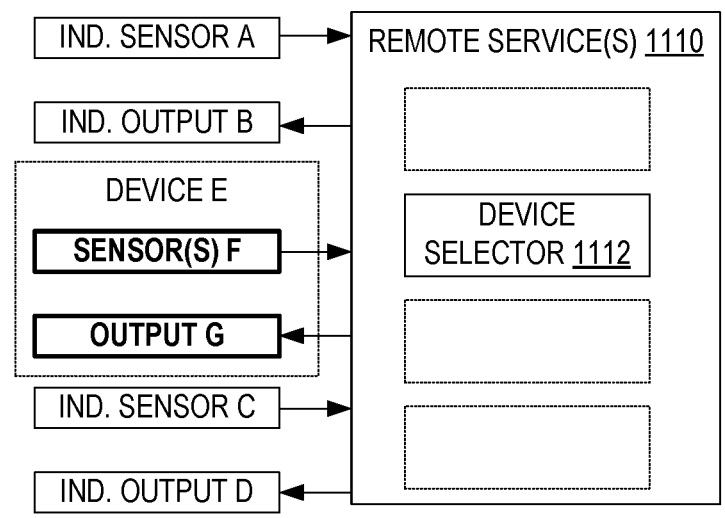
FIG. 12 schematically shows another example implementation in which one or more remote services perform functionality of the intelligent assistant computing system in combination with multiple independent on-premises sensors and/or devices according to examples of the present disclosure.

FIG. 12 shows another example implementation in which one or more remote services 1110 perform the natural language processing functionality of intelligent assistant computing system 200. In this example, the one or more remote services are communicatively coupled with a plurality of different sensors and output devices. In this example, the sensors include individual standalone sensors A and C, such as microphones, cameras, etc. The output devices include individual standalone output devices B and D, such as loudspeakers.

The one or more remote services 1110 are also communicatively coupled to a device E that includes one or more sensors F and an output device G. Device E may take the form of a simple standalone device comprising a microphone, speaker and network connectivity components. In other examples, device E may be a mobile phone, tablet computer, wall-mounted display, or other suitable computing device. In some examples, device E, sensors A and C, and output devices B and D may be part of the same cloud-supported client. In other examples, any number of individual sensors and devices may be utilized with the one or more remote services 1110.

As described above, the one or more remote services 1110 perform the natural language processing functionality of intelligent assistant computing system 200. In some examples, one or more of the remote services 1110 may include all of the natural language processing modules of intelligent assistant computing system 200. In other examples, one or more remote services 1110 may include less than all of the natural language processing modules, and may be communicatively coupled to the other modules located at one or more other service(s). In the present example, and as described in more detail below, one or more of the remote services 1110 also may comprise a device selector 1112 that may utilize sensor inputs to select output device B, D and/or G to receive output from the commitment engine 260.

Figure 13:
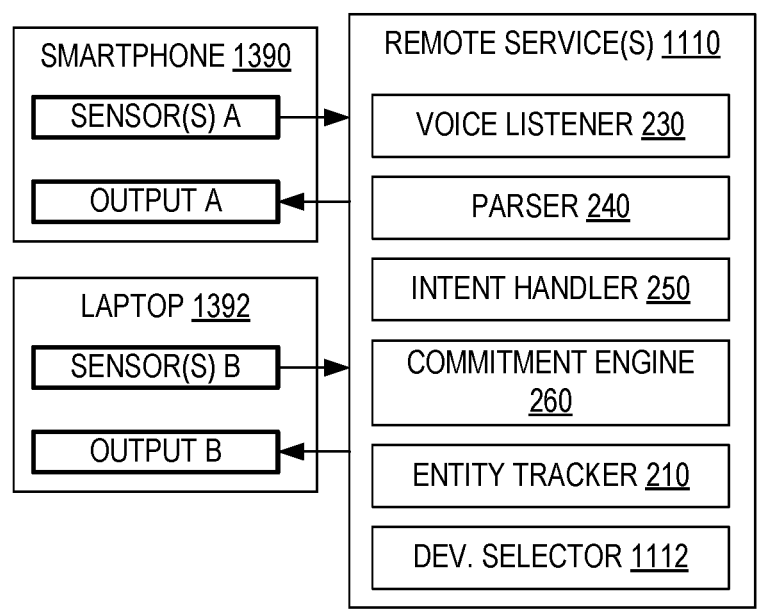
FIG. 13 schematically shows another example implementation in which one or more remote services utilizes a device selector according to examples of the present disclosure.

With reference now to FIG. 13, in some examples the intelligent assistant computing system 200 of the present disclosure may utilize device selector 1112 to enable a user to communicate with another person whose location may be unknown to the user. In some examples, the system may use sensor data and/or corresponding context data to detect the presence and determine the location of the other person. Upon receiving a request from the user to speak to or locate the other person, the device selector 1112 may select an appropriate output device for establishing communication between the user and the other person.

In the example use case of FIG. 13, one or more remote services 1110 implementing intelligent assistant computing system 20 are communicatively coupled with a smartphone 1390 and laptop 1392. In one example, smartphone 1390 comprises multiple sensors A including a microphone, and an output device A in the form of a speaker. The smartphone 1390 may be located with a user in the user's basement media room of her home. The laptop computer 1392 comprises multiple sensors B including a microphone and a webcam, and an output device B in the form of a speaker. The laptop 1392 may be located in an upstairs bedroom of the home.

The user of the smartphone 1390 may desire to communicate with her daughter, but may not know her current location within the home. The daughter may be in the upstairs bedroom with two other friends. The user may speak natural language inputs to indicate that she would like to communicate with her daughter. For example, the user may speak "Connect me to Sarah." The microphone in the user's smartphone 1390 may receive the natural language input and send it to a remote service 1110 for processing by the voice listener 230 and other components of intelligent assistant computing system 200 described above.

Upon determining the intent of the user, the commitment engine 260 may request context information from the entity tracker 210 that includes the location of the user's daughter Sarah. In response, the entity tracker 210 may utilize video data from the webcam of the laptop 1392 to identify Sarah in the field of view of the webcam. Entity tracker 210 may use other context information to determine that the laptop 1392, and thus daughter Sarah, are located in the upstairs bedroom.

Using this information, the device selector 1112 may communicatively couple the microphone and speaker of the user's smartphone 1390 with microphone and speaker of laptop computer 1392, and thereby allow the user to talk with her daughter.

In other examples and as discussed above, one or more other types of sensors and corresponding data may be used to locate a person or other entity. Examples include solely audio data, combinations of video and audio data, device log-in data, and other combinations of the foregoing and other sensor data.

Figure 14:
FIG. 14 schematically shows an example implementation in which one or more functions of the intelligent assistant computing system are activated upon detection of one or more spoken keywords.

With reference now to FIG. 14, in one example one or more sensors 220 in the form of microphones may receive audio data of a user speaking "Hey computer, what time is the school board meeting tonight?" As described above, the voice listener 230 may process the audio data into text and confidence value(s), and pass this information to the parser 240. An attention activator 1432 in parser 240 may identify the keyword phrase "Hey computer" in the text. In response, the parser 240 may activate or modify other components and functionality of the intelligent assistant computing system 200. For example, the parser 240 may increase a sampling rate of a speech recognition module to increase recognition accuracy of the user's speech that is likely to follow.

As noted above, upon processing audio data of a user's natural language input, a commitment engine may provide output to one or more output devices, such as a speaker and/or a video display. In some examples, a single device may include a microphone that captures a user's input, with such input provided to the intelligent assistant computing system 200, and a speaker that receives and broadcasts a message generated by the system in response to the input.

In some examples, a user may be in an environment with two or more microphones that may capture user speech and/or two or more speakers that may broadcast a message generated by the system in response to the speech. For example, a user may be in his media room with his mobile phone, laptop computer, tablet computer, and smart/connected television. Each of these devices may contain or be communicatively coupled with an intelligent assistant computing system 200.

A user may speak a keyword phrase that is captured by the microphones of each of the plurality of devices. Accordingly, the corresponding message generated by the intelligent assistant computing system 200 may be broadcast by the speakers in all devices, which may be annoying to the user. As described in more detail below, in some examples involving multiple sensors, output devices and/or other devices, the intelligent assistant computing system 200 may be configured to determine which of the multiple microphones to use for receiving user speech and/or which of the multiple speakers to use for broadcasting a corresponding message. In some examples and as described below, an aggregator may evaluate and weigh a plurality of metrics to determine which microphones and speakers to utilize.

Figure 15:
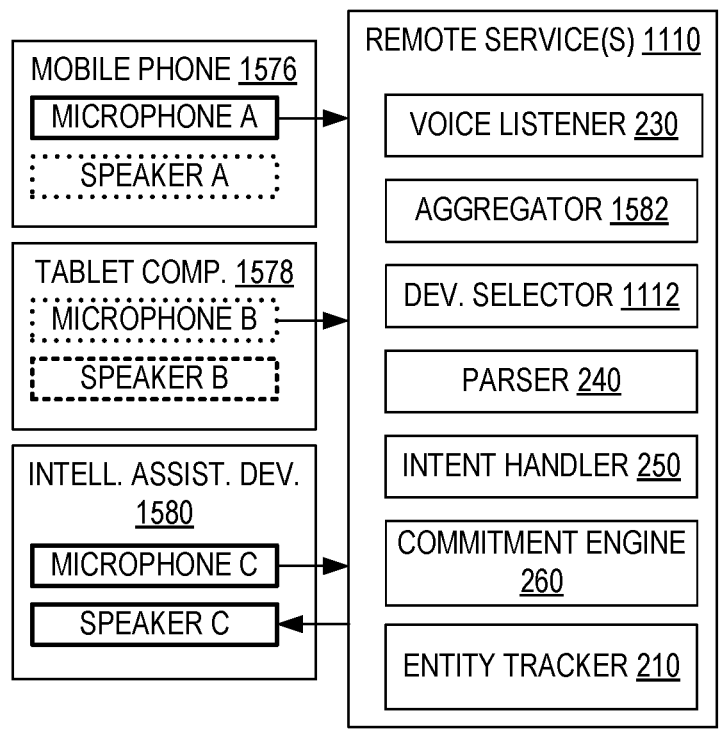
FIG. 15 schematically shows an example implementation of a multi-device environment in which sensor(s) and output device(s) are selected in response to voice activation according to examples of the present disclosure.

With reference now to FIG. 15, an example implementation of sensor and output device selection in response to voice activation in a multi-device environment is provided. In this example, one or more remote services 1110 that implement the intelligent assistant computing system 200 may receive audio data from three different microphones A, B and C of three different devices, such as a mobile phone 1576, tablet computer 1578 and all-in-one intelligent assistant device 1580.

A user in the vicinity of the three devices may speak a keyword phrase, such as "Hey Computer." Each of the microphones A, B and C may capture audio data of the user speaking this phrase and may send the audio data to voice listener 230. As described above, voice listener 230 may utilize speech recognition technologies to translate spoken utterances into text. Voice listener 230 also may assign confidence value(s) to the translated text. In some examples, the voice listener 230 may comprise a keyword detection algorithm configured to identify a keyword or keyword phrase in the translated text. The voice listener 230 may assign a confidence value to text that indicates a likelihood that the text is a keyword or keyword phrase.

In some examples, an aggregator 1582 may evaluate a plurality of metrics related to a plurality of user audio data streams that are received from different individual microphones and/or from different microphone arrays. As described in more detail below, the aggregator 1582 may utilize these metrics to select one of the audio data streams and its corresponding microphone(s) for use in interacting with the user. In some examples, the microphone(s) that is determined to be closest to the user may be selected. In some examples, the microphone(s) that is determined to provide the highest quality audio data may be selected. In some examples, the microphone(s) providing the highest quality audio data may be determined to be the closest microphone(s) to the user, and therefore may be selected.

When a microphone has been selected, the device selector 1112 may select a speaker associated with this microphone to output a response to the user. For example, where the microphone is a component of a device that includes a speaker, this speaker may be selected. Where the microphone is a standalone microphone, the aggregator 1582 may select another speaker in the vicinity of the user to output the response. In the example of FIG. 15, the aggregator 1582 is located on one of the remote services that implements at least a portion of the intelligent assistant computing system 200. In other examples, the aggregator 1582 may be located on another computing device, such as in another cloud-based service.

In one use case example, the aggregator 1582 may utilize four metrics to evaluate a user audio data stream that is received: (1) an amplitude (volume) of the received audio signal; (2) a signal-to-noise (S/N) ratio of the audio signal; (3) a keyword confidence value indicating a likelihood that the data stream contains a keyword or keyword phrase; and (4) a user identification confidence value indicating a likelihood that the speaker is a particular person.

In some examples, the amplitude and/or S/N values may be received with the audio data stream. In other examples, amplitude and/or S/N values may be determined by the voice listener 230 or other components of the intelligent assistant computing system 200. As described above, the keyword confidence value may be determined by the voice listener 230. Also as described above, the user identification confidence value may be determined by entity tracker 210. In some examples, the user speaking the input may be identified by voice recognition as a known speaker or an unknown speaker, and assigned a corresponding level of confidence.

The S/N ratio may be calculated for the received audio input by comparing a signal level of a user's voice to a level of background noise. In some examples the amplitude of the input may be used to determine a proximity of the user to the corresponding microphone. It will be appreciated that the metrics discussed in the present implementations are provided as examples and are not meant to be limiting.

Each of the received audio data streams also may include a device ID that identifies the particular device or standalone sensor that is providing the data stream. In some examples, after receiving a first set of metrics from a first device or sensor, the aggregator 1582 may pause for a predetermined period of time to determine if one or more other devices/sensors also received the keyword or keyword phrase from the same person as the user identified in the first set of metrics. For example, the aggregator 1582 may pause for 0.5 seconds, 1.0 seconds, or any other period of time that does not create a negative user experience for the user.

In the present example and as shown in FIG. 15, the aggregator 1582 evaluates metrics for audio data streams received from the mobile phone 1576, tablet computer 1578 and all-in-one intelligent assistant device 1580. For each device, the aggregator 1582 may combine the four metrics into a single selectability score, such as by averaging the four metrics. In some examples and prior to combining, each of the metrics may be weighted by empirically-determined weights that reflect the accuracy of a metric in predicting the device/microphone and corresponding audio data stream that will provide the best user experience. By comparing the selectability scores of each of the devices/microphones and their data streams, the aggregator 1582 may identify and select the desired device/data stream.

In one example, for each of the four metrics, the aggregator 1582 may compare the scores of each device/microphone and correspondingly rank the devices/microphone per metric. For example, the aggregator 1582 may determine the following scores for the audio data stream received from microphone A of the mobile phone 1576: 1) 90% (Amplitude); 2) 90% (S/N); 3) 30% (Keyword confidence); 4) 90% (Speaker ID). Scores for the audio data stream received from microphone B of the tablet computer 1578 may be: 1) 80% (Amplitude); 2) 80% (S/N); 3) 80% (Keyword confidence); 4) 80% (Speaker ID). Scores for the audio data stream received from the microphone C of the intelligent assistant device 1580 may be: 1) 92% (Amplitude); 2) 88% (S/N); 3) 90% (Keyword confidence); 4) 92% (Speaker ID).

In this example, the rankings of the three devices for each of the four metrics would be as follows:
  A. Amplitude—1. Intelligent assistant device; 2. Mobile phone; 3. Tablet computer.
  B. S/N Ratio—1. Mobile phone; 2. Intelligent assistant device; 3. Tablet computer.
  C. Keyword Confidence—1. Intelligent assistant device; 2. Tablet computer; 3. Mobile phone.
  D. Speaker ID—1. Intelligent assistant device; 2. Mobile phone; 3. Tablet computer.

Each device may be awarded points based on its ranking in each metric category. For example, a first place ranking=1 point, second place=2 points and third place=3 points. For each device, its points are totaled for the four metrics and averaged. The aggregator 1582 selects the device (and corresponding data stream) with the lowest average point total. In the present example, the final point totals and rankings are: 1. Intelligent assistant device=>1.25; 2. Mobile phone=>2.0; 3. Tablet computer=>2.75. Thus, the aggregator 1582 selects the data stream from the intelligent assistant device 1580 for continued analysis by the intelligent assistant computing system 200. Additionally, and based on the above ranking, the device selector 1112 may select the intelligent assistant device 1580 to receive the message(s) generated by commitment engine 260 as a result of the analysis.

In some examples, upon selection by the aggregator 1582 of the intelligent assistant device 1580 as described above, the aggregator also may cause the other two devices to refrain from sending audio data streams that are associated with the same speaker ID (i.e., person) that is associated with the analyzed data stream. In this manner, where the same user provides more natural language input after the initial input, only the selected intelligent assistant device 1580 will provide the corresponding audio data to the remote service(s) 1110. In some examples, the other two devices may resume sending audio data streams when the same person speaks the keyword or keyword phrase. In these cases, the above-described selection process may be performed again to determine the selected device.

In some examples and as noted above, prior to averaging the awarded points, each point award may be multiplied by an empirically-determined weighted value that reflects the accuracy of a metric in predicting the device and corresponding audio data stream that will provide the best user experience. In some examples, one or more machine learning techniques may be utilized to build models for computing the different metrics.

In some example implementations, the signal amplitude may strongly correlate to a user's distance from the microphone receiving the user's speech. The S/N ratio also may provide a good indicator of the user's distance from the microphone, as a lower noise value may correlate to the user being closer to the microphone. Where the signal amplitude and S/N ratio of the signal are both relatively high, the speaker ID accuracy may correspondingly benefit from the strong signal.

It will be appreciated that the methods and use cases described above are merely examples, and many variations are possible. For example, a subset of the above four metrics may be utilized to evaluate a user audio data stream. In other examples, one or more additional metrics also may be utilized.

In some examples, a user who has previously established a conversation with the intelligent assistant computing system 200 via a selected device among multiple devices may have a brief pause before initiating a next conversation with the same device. The system may compare the duration of the pause to a predetermined time period, and may consider the comparison in selecting a device for the next conversation. For example, where the duration of the pause is less than the predetermined period, such as 5 seconds, the system may include the recently-established speaker ID and the existence of the previous conversation in the device determination analysis as a bias towards selecting the same device for the next conversation.

The examples described above include recognition of an audible keyword to activate one or more functions of the intelligent assistant computing system. In some examples, functions of the system may be activated by recognition of one or more other signals. Such signals may include, for example, a user gesture captured by a camera, a user eye-gaze, and a face direction of the user.

In some examples, one or more of the above-described techniques for device selection may be utilized to automatically update the selected device based on one or more factors. For example, where a user is communicating with the intelligent assistant computing system 200 via a first device, as the user changes her location and moves farther away from the first device, the system may correspondingly change the selected device to a second device closer to the user's new location.

In some implementations, imaging data in addition to audio data from one or more image sensors may be utilized to select a device. For example, context information 810 received from entity tracker 210 may include imaging data that may be used to select a device. Examples of imaging data may include video from an RGB camera, infrared images from an IR camera, depth images from a depth camera, thermal images from a thermal camera, etc. For example, an RGB camera may track a user's location within a room. Images from the camera may be used to select the appropriate device/microphone(s) to receive the user's natural language input, and/or to select the appropriate speaker(s) to broadcast a message to the user. In some examples and with reference to the device selection techniques described above, imaging data and related parameters may be included as a metric that is analyzed by the aggregator 1582 to determine device selection.

In some examples, captured images of a user may be used to identify which device a user is facing when speaking. In some examples, indicators such as face detection may be used to identify a user. In some examples, captured video may indicate lip movement of a user that may be used to associate a spoken keyword with the user. In an environment with multiple users, such indicators also may identify the particular user who is addressing a device. As such, both voice and physical recognition may be used as parameters to distinguish a user from among the plurality of users.

Other examples of inputs that may be used in selecting a device/microphone and/or speaker include radar signals and lidar signals. In some examples, signals from connected devices may indicate that a user is interacting with the device. In one example, a user may activate a mobile phone via fingerprint recognition. Such an interaction may be a strong indicator that the user is present at the location of the phone.

In some embodiments, the methods and processes described herein may be tied to a computing system of one or more computing devices. In particular, such methods and processes may be implemented as a computer-application program or service, an application-programming interface (API), a library, and/or other computer-program product.

Figure 16:
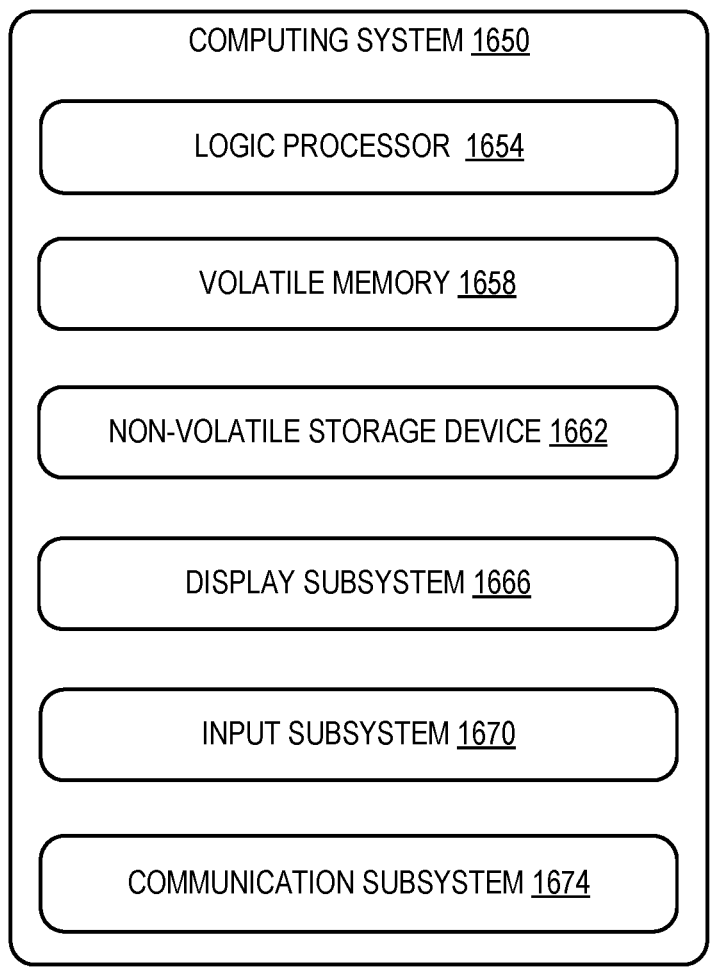
FIG. 16 schematically shows a computing system according to examples of the present disclosure.

FIG. 16 schematically shows a non-limiting embodiment of a computing system 1650 that can enact one or more of the methods and processes described above. Computing system 1650 is shown in simplified form. Computing system 1650 may take the form of one or more personal computers, server computers, tablet computers, home-entertainment computers, network computing devices, gaming devices, mobile computing devices, mobile communication devices (e.g., smartphone), and/or other computing devices.

Computing system 1650 includes a logic processor 1654, volatile memory 1658, and a non-volatile storage device 1662. Computing system 1650 may optionally include a display subsystem 1666, input subsystem 1670, communication subsystem 1674, and/or other components not shown in FIG. 16.

Logic processor 1654 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor 1654 may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 1654 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor 1654 may be virtualized and executed by remotely accessible, networked computing devices configured in a cloud-computing configuration. In such a case, these virtualized aspects may be run on different physical logic processors of various different machines.

Volatile memory 1658 may include physical devices that include random access memory. Volatile memory 1658 is typically utilized by logic processor 1654 to temporarily store information during processing of software instructions. It will be appreciated that volatile memory 1658 typically does not continue to store instructions when power is cut to the volatile memory.

Non-volatile storage device 1662 includes one or more physical devices configured to hold instructions executable by the logic processors to implement the methods and processes described herein. When such methods and processes are implemented, the state of non-volatile storage device 1662 may be transformed—e.g., to hold different data. Non-volatile device 1662 may also hold data, including the various data items described herein. Such data may be organized in one or more databases that collectively form a database system. One or more data holding devices of storage device 1662 may be referred to collectively as a data storage system. While various data items are referred to as being stored in or at a data storage system or data storage device, it will be understood that such data items may be distributed across two or more data storage devices. Accordingly, data items that are referred to as being associated with a person profile, for example, may be stored in different data storage devices and/or using two or more databases that collectively form a database system.

Non-volatile storage device 1662 may include physical devices that are removable and/or built-in. Non-volatile storage device 1662 may include optical memory (CD, DVD, HD-DVD, Blu-Ray Disc, etc.), semiconductor memory (ROM, EPROM, EEPROM, FLASH memory, etc.), and/or magnetic memory (hard-disk drive, floppy-disk drive, tape drive, MRAM, etc.), or other mass storage device technology. Non-volatile storage device 1662 may include nonvolatile, dynamic, static, read/write, read-only, sequential-access, location-addressable, file-addressable, and/or content-addressable devices. It will be appreciated that non-volatile storage device 1662 is configured to hold instructions even when power is cut to the non-volatile storage device.

Aspects of logic processor 1654, volatile memory 1658, and non-volatile storage device 1662 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module", "program" and "engine" may be used to describe an aspect of computing system 1650 implemented to perform a particular function. In some cases, a module, program or engine may be instantiated via logic processor 1654 executing instructions held by non-volatile storage device 1662, using portions of volatile memory 1658. It will be understood that different modules, programs or engines may be instantiated from the same application, service, code block, object, library, routine, API, function, etc. Likewise, the same module, program or engine may be instantiated by different applications, services, code blocks, objects, routines, APIs, functions, etc. The terms modules, programs and engines encompass individual or groups of executable files, data files, libraries, drivers, scripts, database records, etc.

It will be appreciated that a "service", as used herein, is an application program that may be executable across multiple user sessions. A service may be available to one or more system components, programs, and/or other services. In some implementations, a service may run on one or more server-computing devices.

When included, display subsystem 1666 may be used to present a visual representation of data held by non-volatile storage device 1662. As the herein described methods and processes change the data held by the non-volatile storage device, and thus transform the state of the non-volatile storage device, the state of display subsystem 1666 may likewise be transformed to visually represent changes in the underlying data. Display subsystem 1666 may include one or more display devices utilizing virtually any type of technology. Such display devices may be combined with logic processor 1654, volatile memory 1658, and/or non-volatile storage device 1662 in a shared enclosure, or such display devices may be peripheral display devices.

When included, input subsystem 1670 may comprise or interface with one or more user-input devices. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection, gaze detection, and/or intent recognition; electric-field sensing componentry for assessing brain activity; any of the sensors described with respect to the example use cases and environments discussed above; and/or any other suitable sensor.

When included, communication subsystem 1674 may be configured to communicatively couple computing system 1650 with one or more other computing devices. Communication subsystem 1674 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 1650 to send and receive data to and from other devices via a network such as the Internet.

In accordance with an example implementation of the present disclosure, a method performed by a computing system for registering a person with an intelligent assistant computer includes: obtaining one or more image frames captured via one or more cameras that depict an initially unregistered person; extracting facial recognition data for the initially unregistered person from the one or more image frames; receiving a spoken command to register the initially unregistered person via one or more microphones; determining that the spoken command originated from a registered person having a pre-established registration privilege; and upon determining that the spoken command originated from the registered person having the pre-established registration privilege, registering the initially unregistered person as a newly registered person by associating one or more additional privileges with the facial recognition data in a person profile for the newly registered person. In this or any other implementation disclosed herein, the one or more image frames are captured after receiving the spoken command to register the initially unregistered person. In this or any other implementation disclosed herein, the method further includes responsive to receiving the spoken command to register the initially unregistered person, directing the initially unregistered person to position its face within a field of view of the one or more cameras to capture the one or more image frames for facial recognition. In this or any other implementation disclosed herein, directing the initially unregistered person includes one or more of outputting an audible direction via an audio speaker and/or outputting a visual direction via a graphical display device. In this or any other implementation disclosed herein, the method further includes responsive to receiving the spoken command to register the initially unregistered person, directing the initially unregistered person to speak one or more words or phrases; obtaining one or more audio segments captured via one or more microphones that include the one or more words or phrases spoken by the initially unregistered person; extracting speaker recognition data from the one or more audio segments for the initially unregistered person; and associating the speaker recognition data with the person profile for the newly registered person. In this or any other implementation disclosed herein, the spoken command to register the initially unregistered person is received after the one or more image frames are captured via the one or more cameras. In this or any other implementation disclosed herein, the method further includes storing the one or more image frames in a data storage system prior to receiving the spoken command to register the initially registered person; retrieving the one or more image frames from the data storage system; presenting the one or more image frames via a graphical display device for review by the registered person; and wherein the spoken command is received during or after presentation of the one or more image frames. In this or any other implementation disclosed herein, the one or more image frames are presented after the initially unregistered person leaves a field of view of the one or more cameras. In this or any other implementation disclosed herein, the one or more image frames are presented responsive to another command initiated by the registered person. In this or any other implementation disclosed herein, the one or more image frames form part of one or more video segments captured via the one or more cameras; and the method further includes: identifying a speaking activity of the initially unregistered person within the one or more video segments; obtaining one or more audio segments, captured via one or more microphones, that are time-matched to the one or more video segments; extracting speaker recognition data for the initially unregistered person from the one or more audio segments based on one or more spoken words or phrases that correspond to the speaking activity of the initially unregistered person; and associating the speaker recognition data with the person profile. In this or any other implementation disclosed herein, the method further includes: receiving a subsequent spoken command to perform one or more operations via one or more microphones; determining that the subsequent spoken command originated from the newly registered person having the one or more additional privileges based on the speaker recognition data; and performing an operation of the one or more operations that is permitted by the one or more additional privileges responsive to the spoken command. In this or any other implementation disclosed herein, the spoken command forms part of a spoken phrase that originated from the registered person that further includes a person identifier for the newly registered person; and the method further includes associating the person identifier with the person profile for the newly registered person. In this or any other implementation disclosed herein, the spoken command forms part of a spoken phrase that originated from the registered person that further includes a privileges identifier for the newly registered person that identifies the one or more additional privileges associated with the person profile; wherein each privilege of the one or more additional privileges permits one or more operations, not previously permitted prior to registration, to be performed by the intelligent assistant computer responsive to a command originating from the newly registered person. In this or any other implementation disclosed herein, the privilege identifier indicates whether the newly registered person is permitted to register other initially unregistered persons.

In accordance with another example implementation of the present disclosure, a computing system includes one or more cameras to capture image data; one or more microphones to capture audio data; one or more computing devices implementing an intelligent assistant service configured to: obtain one or more image frames captured via the one or more cameras that depict an initially unregistered person; extract facial recognition data for the initially unregistered person from the one or more image frames; receive a spoken command to register the initially unregistered person via the one or more microphones; determine that the spoken command originated from a registered person having a pre-established registration privilege; and upon determining that the spoken command originated from the registered person having the pre-established registration privilege, register the initially unregistered person as a newly registered person by associating one or more additional privileges with the facial recognition data in a person profile for the newly registered person stored in a data storage system of the one or more computing devices. In this or any other implementation disclosed herein, the one or more image frames are captured after receiving the spoken command to register the initially unregistered person; and wherein the intelligent assistant service is further configured to: responsive to receiving the spoken command to register the initially unregistered person, direct the initially unregistered person to position its face within a field of view of the one or more cameras to capture the one or more image frames for facial recognition. In this or any other implementation disclosed herein, the intelligent assistant service is further configured to: responsive to receiving the spoken command to register the initially unregistered person, direct the initially unregistered person to speak one or more words or phrases; obtain one or more audio segments captured via the one or more microphones that include the one or more words or phrases spoken by the initially unregistered person; extract speaker recognition data from the one or more audio segments for the initially unregistered person; and associate the speaker recognition data with the person profile for the newly registered person. In this or any other implementation disclosed herein, the spoken command to register the initially unregistered person is received after the one or more image frames are captured via the one or more cameras; and wherein the intelligent assistant service is further configured to: store the one or more image frames in the data storage system prior to receiving the spoken command to register the initially registered person; retrieve the one or more image frames from the data storage system after the initially unregistered person leaves a field of view of the one or more cameras; present the one or more image frames via a graphical display device for review by the registered person; and wherein the spoken command is received during or after presentation of the one or more image frames. In this or any other implementation disclosed herein, the intelligent assistant service is further configured to: receive a subsequent spoken command to perform one or more operations via the one or more microphones; determine that the subsequent spoken command originated from the newly registered person having the one or more additional privileges; and perform an operation that is permitted by the one or more additional privileges responsive to the spoken command.

In accordance with another example implementation of the present disclosure, a method performed by a computing system for registering a person with an intelligent assistant computer includes: obtaining one or more image frames captured via one or more cameras that depict an initially unregistered person; extracting facial recognition data for the initially unregistered person from the one or more image frames; obtaining one or more audio segments captured via one or more microphones that include one or more words and/or phrases spoken by the initially unregistered person; extracting speaker recognition data for the initially unregistered person from the one or more audio segments; receiving a spoken command to register the initially unregistered person via one or more microphones; determining that the spoken command originated from a registered person having a pre-established registration privilege; upon determining that the spoken command originated from the registered person having the pre-established registration privilege, registering the initially unregistered person as a newly registered person by associating one or more additional privileges with the facial recognition data and the voice recognition data in a person profile for the newly registered person; following registration of the newly registered person, receiving a subsequent spoken command to perform one or more operations via the one or more microphones; determining that the subsequent spoken command originated from the newly registered person having the one or more additional privileges based on the speaker recognition data; and performing an operation that is permitted by the one or more additional privileges responsive to the spoken command.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A method performed by a computing system for registering a person with an intelligent assistant computer, the method comprising:
obtaining one or more image frames captured via one or more cameras that depict an initially unregistered person;
extracting facial recognition data for the initially unregistered person from the one or more image frames;
receiving a spoken command to register the initially unregistered person via one or more microphones;
determining that the spoken command originated from a registered person having a pre-established registration privilege; and
upon determining that the spoken command originated from the registered person having the pre-established registration privilege, registering the initially unregistered person as a newly registered person by associating one or more additional privileges with the facial recognition data in a person profile for the newly registered person.

2. The method of claim 1, wherein the one or more image frames are captured after receiving the spoken command to register the initially unregistered person.

3. The method of claim 2, further comprising:
responsive to receiving the spoken command to register the initially unregistered person, directing the initially unregistered person to position its face within a field of view of the one or more cameras to capture the one or more image frames for facial recognition.

4. The method of claim 3, wherein directing the initially unregistered person includes one or more of outputting an audible direction via an audio speaker and/or outputting a visual direction via a graphical display device.

5. The method of claim 1, further comprising:
responsive to receiving the spoken command to register the initially unregistered person, directing the initially unregistered person to speak one or more words or phrases;
obtaining one or more audio segments captured via one or more microphones that include the one or more words or phrases spoken by the initially unregistered person;
extracting speaker recognition data from the one or more audio segments for the initially unregistered person; and
associating the speaker recognition data with the person profile for the newly registered person.

6. The method of claim 1, wherein the spoken command to register the initially unregistered person is received after the one or more image frames are captured via the one or more cameras.

7. The method of claim 6, further comprising:
storing the one or more image frames in a data storage system prior to receiving the spoken command to register the initially registered person;
retrieving the one or more image frames from the data storage system;
presenting the one or more image frames via a graphical display device for review by the registered person; and
wherein the spoken command is received during or after presentation of the one or more image frames.

8. The method of claim 7, wherein the one or more image frames are presented after the initially unregistered person leaves a field of view of the one or more cameras.

9. The method of claim 7, wherein the one or more image frames are presented responsive to another command initiated by the registered person.

10. The method of claim 1, wherein the one or more image frames form part of one or more video segments captured via the one or more cameras; and
wherein the method further comprises:
identifying a speaking activity of the initially unregistered person within the one or more video segments;
obtaining one or more audio segments, captured via one or more microphones, that are time-matched to the one or more video segments;
extracting speaker recognition data for the initially unregistered person from the one or more audio segments based on one or more spoken words or phrases that correspond to the speaking activity of the initially unregistered person; and
associating the speaker recognition data with the person profile.

11. The method of claim 10, further comprising:
receiving a subsequent spoken command to perform one or more operations via one or more microphones;
determining that the subsequent spoken command originated from the newly registered person having the one or more additional privileges based on the speaker recognition data; and
performing an operation of the one or more operations that is permitted by the one or more additional privileges responsive to the spoken command.

12. The method of claim 1, wherein the spoken command forms part of a spoken phrase that originated from the registered person that further includes a person identifier for the newly registered person; and wherein the method further comprises associating the person identifier with the person profile for the newly registered person.

13. The method of claim 1, wherein the spoken command forms part of a spoken phrase that originated from the registered person that further includes a privileges identifier for the newly registered person that identifies the one or more additional privileges associated with the person profile;

wherein each privilege of the one or more additional privileges permits one or more operations, not previously permitted prior to registration, to be performed by the intelligent assistant computer responsive to a command originating from the newly registered person.

14. The method of claim 13, wherein the privilege identifier indicates whether the newly registered person is permitted to register other initially unregistered persons.

15. A computing system, comprising:
one or more cameras to capture image data;
one or more microphones to capture audio data;
one or more computing devices implementing an intelligent assistant service configured to:
obtain one or more image frames captured via the one or more cameras that depict an initially unregistered person;
extract facial recognition data for the initially unregistered person from the one or more image frames;
receive a spoken command to register the initially unregistered person via the one or more microphones;
determine that the spoken command originated from a registered person having a pre-established registration privilege; and
upon determining that the spoken command originated from the registered person having the pre-established registration privilege, register the initially unregistered person as a newly registered person by associating one or more additional privileges with the facial recognition data in a person profile for the newly registered person stored in a data storage system of the one or more computing devices.

16. The computing system of claim 15, wherein the one or more image frames are captured after receiving the spoken command to register the initially unregistered person; and wherein the intelligent assistant service is further configured to:
responsive to receiving the spoken command to register the initially unregistered person, direct the initially unregistered person to position its face within a field of view of the one or more cameras to capture the one or more image frames for facial recognition.

17. The computing system of claim 15, wherein the intelligent assistant service is further configured to:
responsive to receiving the spoken command to register the initially unregistered person, direct the initially unregistered person to speak one or more words or phrases;
obtain one or more audio segments captured via the one or more microphones that include the one or more words or phrases spoken by the initially unregistered person;
extract speaker recognition data from the one or more audio segments for the initially unregistered person; and associate the speaker recognition data with the person profile for the newly registered person.

18. The computing system of claim 15, wherein the spoken command to register the initially unregistered person is received after the one or more image frames are captured via the one or more cameras; and wherein the intelligent assistant service is further configured to:
store the one or more image frames in the data storage system prior to receiving the spoken command to register the initially registered person;
retrieve the one or more image frames from the data storage system after the initially unregistered person leaves a field of view of the one or more cameras;
present the one or more image frames via a graphical display device for review by the registered person; and
wherein the spoken command is received during or after presentation of the one or more image frames.

19. The computing system of claim 15, wherein the intelligent assistant service is further configured to:
receive a subsequent spoken command to perform one or more operations via the one or more microphones;
determine that the subsequent spoken command originated from the newly registered person having the one or more additional privileges; and
perform an operation that is permitted by the one or more additional privileges responsive to the spoken command.

20. A method performed by a computing system for registering a person with an intelligent assistant computer, the method comprising:
obtaining one or more image frames captured via one or more cameras that depict an initially unregistered person;
extracting facial recognition data for the initially unregistered person from the one or more image frames;
obtaining one or more audio segments captured via one or more microphones that include one or more words and/or phrases spoken by the initially unregistered person;
extracting speaker recognition data for the initially unregistered person from the one or more audio segments;
receiving a spoken command to register the initially unregistered person via one or more microphones;
determining that the spoken command originated from a registered person having a pre-established registration privilege;
upon determining that the spoken command originated from the registered person having the pre-established registration privilege, registering the initially unregistered person as a newly registered person by associating one or more additional privileges with the facial recognition data and the voice recognition data in a person profile for the newly registered person;
following registration of the newly registered person, receiving a subsequent spoken command to perform one or more operations via the one or more microphones;
determining that the subsequent spoken command originated from the newly registered person having the one or more additional privileges based on the speaker recognition data; and
performing an operation that is permitted by the one or more additional privileges responsive to the spoken command.

* * * * *